United States Patent [19]

Okamura et al.

[11] 4,421,914
[45] Dec. 20, 1983

[54] THIAZOLO[3,2-A]PYRIMIDINES, DERIVATIVES THEREOF, PROCESSES FOR PRODUCTION THEREOF, AND PHARMACEUTICAL USE THEREOF

[75] Inventors: Noriaki Okamura, Chofu; Takeshi Toru, Hachioji; Takeo Ōba, Hino; Toshio Tanaka, Hino; Kiyoshi Bannai, Hino; Kenzo Watanabe, Hino; Seizi Kurozumi, Kokubunji; Tatsuyuki Naruchi, Hino; Keiji Komoriya, Hachioji, all of Japan

[73] Assignee: Teijin Limited, Tokyo, Japan

[21] Appl. No.: 311,329

[22] Filed: Oct. 14, 1981

[30] Foreign Application Priority Data

Oct. 15, 1980 [JP] Japan .................... 55-142869
Aug. 10, 1981 [JP] Japan .................... 56-124173

[51] Int. Cl.³ .............. C07D 513/14; A61K 31/505
[52] U.S. Cl. ........................ 544/278; 544/282; 544/117; 424/251; 424/248.4
[58] Field of Search .............................. 544/278, 282

[56] References Cited

FOREIGN PATENT DOCUMENTS

| 55-62092 | of 1980 | Japan | 544/278 |
|---|---|---|---|
| 55-62093 | of 1980 | Japan | 544/278 |
| 55-64591 | of 1980 | Japan | 544/278 |
| 55-64592 | of 1980 | Japan | 544/278 |
| 55-66592 | of 1980 | Japan | 544/278 |
| 55-66593 | of 1980 | Japan | 544/278 |
| 55-115889 | of 1980 | Japan | 544/278 |
| 55-136293 | of 1980 | Japan | 544/278 |
| 638504 | 6/1950 | United Kingdom | 544/278 |

OTHER PUBLICATIONS

Journal of American Chem. Soc. 64 1942, 2709–2712.

Primary Examiner—Mark L. Berch
Assistant Examiner—S. A. Gibson
Attorney, Agent, or Firm—Wenderoth, Lind & Ponack

[57] ABSTRACT

A compound selected from thiazolo[3,2-a]pyrimidines or their enolate derivatives represented by the following general formula

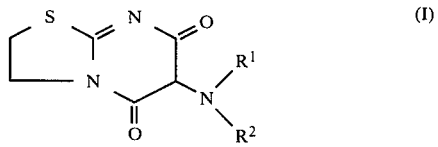

wherein $R^1$ and $R^2$ are identical or different, and each represents a hydrogen atom, an alkyl group having 1 to 10 carbon atoms, an alkenyl group having 3 to 10 carbon atoms, a substituted or unsubstituted phenyl group, a substituted or unsubstituted cycloaliphatic group having 3 to 8 carbon atoms, a substituted or unsubstituted phenylalkyl group or a substituted or unsubstituted acyl group having 2 to 7 carbon atoms, provided that $R^1$ and $R^2$ are not simultaneously hydrogen atoms or substituted or unsubstituted acyl groups having 2 to 7 carbon atoms; and $R^1$ and $R^2$, when taken together, may form, with the nitrogen atom to which they are bonded, a 5- or 6-membered ring which may further contain one or more hetero atoms;

and acid addition salts of these compounds.

The thiazolo[3,2-a]pyrimidines may be prepared by a process comprising (a) reacting a malonic acid derivative of the following general formula

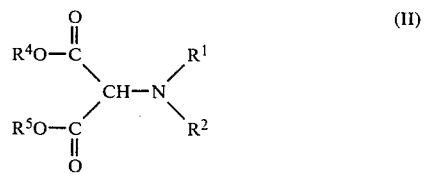

wherein $R^1$ and $R^2$ are as defined with regard to formula (I), and $R^4$ and $R^5$ are identical or different and each represents an alkyl group having 1 to 6 carbon atoms, with 2-aminothiazoline under heat, if desired in the presence of an inert organic solvent, to induce cyclocondensation, or (b) performing said condensation reaction in the presence of an alkali metal alkoxide, if desired in the presence of an inert organic solvent, and neutralizing the resulting enolate with an acid; and if desired, reacting the reaction product of (a) or (b) with an acid.

The present invention provides also several processes for preparing enolate derivatives thereof.

The thiazolo[3,2-a]pyrimidines, their enolate derivatives and acid addition compounds thereof are useful for regulating the immune function of a warm-blooded animal.

2 Claims, No Drawings

THIAZOLO[3,2-A]PYRIMIDINES, DERIVATIVES THEREOF, PROCESSES FOR PRODUCTION THEREOF, AND PHARMACEUTICAL USE THEREOF

This invention relates to novel thiazolo[3,2-a]-pyrimidines and their derivatives, processes for production thereof, and their pharmaceutical use. More specifically, it relates to novel thiazolo[3,2-a]pyrimidines having a substituted amino group at the 6-position or their enolate derivatives or the acid addition salts of these, processes for production thereof, and their pharmaceutical use, particularly as an immune regulating agent.

6-Mono- or 6,6-di-substituted-5H-2,3,6,7-tetrahydro-5,7-dioxo-5-thiazolo[3,2 -a]pyrimidines of the following formula

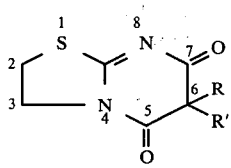

wherein R is hydrogen or ethyl, and R' represents methyl, ethyl, iso-propyl, phenyl or benzyl when R is hydrogen, and ethyl, iso-propyl, n-butyl, phenyl or benzyl when R is ethyl, which are obtained from 2-aminopyrimidine and the corresponding diethyl malonates have previously been known as the thiazolopyrimidines (Journal of American Chemical Society, Vol. 64, 1942, pages 2709-2712). This literature reference states that the above thiazolopyrimidines might be expected to have hypnotic or anesthetic activity.

Japanese Laid-Open Patent Publication No. 64591/1980 claims in its main claim thiazolo[3,2-a]pyrimidine derivatives of the following formula

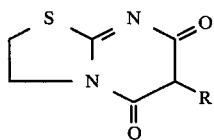

wherein R represents a substituted or unsubstituted alicyclic group, a substituted phenyl group, a substituted aralkyl group, or an unsubstituted aralkyl group having not more than 8 carbon atoms.

Japanese Laid-Open Patent Publication No. 66592/1980 claims in its main claim 7-alkoxythiazolo-[3,2-a]pyrimidine derivatives of the following formula

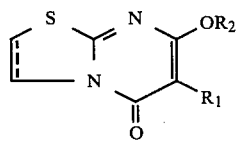

wherein $R_1$ represents a substituted or unsubstituted alicyclic group, a substituted or unsubstituted phenyl group or a substituted or unsubstituted aralkyl group, and $R_2$ represents a lower alkyl group, and the dotted line, taken in conjuction with the solid line, represents a single or double bond.

The two Japanese patent documents cited above disclose that the thiazolo[3,2-a]pyrimidine derivatives claimed have immune regulating activity, particularly immune potentiating activity, when evaluated by a test of delayed type hypersensitivity.

The thiazolo[3,2-a]pyrimidine derivatives disclosed in these two Japanese patent documents have a hydrocarbon group as a substitutent at the 6-position, and in this regard, differ in molecular structure from the novel thiazolo[3,2-a]pyrimidines and their enolate derivatives in accordance with this invention. In addition, the compounds of the invention having a substituted amino group at the 6-position have different immune regulating activity from the aforesaid known compounds having a hydrocarbon group at the 6-position.

Generally, the result of evaluating the immune regulating activity of a given compound differs depending upon systems in which it is assayed. Frequently, the compound is seen to exhibit immune potentiating activity in one assay system, but immune supressing activity in another. For accurate evaluation of the immune regulating activity of a compound, therefore, it is desirable to use as many assay systems as possible.

Investigations of the present inventors have shown that by a plaque forming cells (PFC) test, the compounds having a hydrocarbon group at the 6-position as disclosed in the two Japanese patent documents show immune supressing activity rather than immune potentiating activity.

In contrast, the compounds of the invention having a substituted amino group at the 6-position have been found to exhibit immune potentiating action by the test of delayed type hypersinsitivity and the PFC test, and differ in immune regulating activity from the aforesaid known compounds.

It is an object of this invention therefore to provide novel thiazolo[3,2-a]pyrimidines having a substituted amino group at the 6-position, their enolate derivatives, or the acid addition salts of these compounds.

Another object of this invention is to provide novel thiazolo[3,2-a]pyrimidines, their enolate derivatives, or the acid addition salts of these compounds which have different immune regulating activity from the thiazolo[3,2-a]pyrimidine derivatives having a hydrocarbon group at the 6-position.

Still another object of this invention is to provide immune regulating agents comprising said novel compounds which have the ability to potentiate immune.

A further object of this invention is to provide processes for producing said novel compounds.

Other objects and advantages of the invention will become apparent from the following description.

According to one aspect of the invention, these objects and advantages are achieved by a compound selected from thiazolo[3,2-a]pyrimidines of the following formula

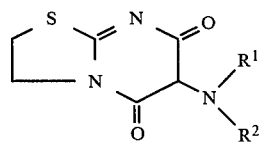

(I)

wherein $R^1$ and $R^2$ are identical or different and each respresents a hydrogen atom, an alkyl group having 1 to 10 carbon atoms, an alkenyl group having 3 to 10 carbon atoms, a substituted or unsubstituted phenyl group, a substituted or unsubstituted cycloaliphatic group having 3 to 8 carbon atoms, a substituted or unsubstituted phenylalkyl group, or a substituted or unsubstituted acyl group having 2 to 7 carbon atoms, provided that $R^1$ and $R^2$ are not simultaneously hydrogen atoms or substituted or unsubstituted acyl groups having 2 to 7 carbon atoms; and $R^1$ and $R^2$, taken together may form, with the nitrogen atom to which they are bonded, a 5- or 6-membered ring which may further contain one or more hetero atoms, their enolate derivative and the acid addition salts of these compounds.

The alkyl group having 1 to 10 carbon atoms, for the groups $R^1$ and $R^2$ may be linear or branched, and includes, for example, methyl, ethyl, n-propyl, iso-propyl, n-butyl, iso-butyl, tert-butyl, n-pentyl, n-hexyl, n-octyl, n-nonyl, and n-decyl. Alkyl groups having 1 to 6 carbon atoms, especially methyl, ethyl, propyl and butyl, are preferred.

The alkenyl group having 3 to 10 carbon atoms may be linear or branched, and includes, for example, allyl, 2-butenyl, 3-butenyl, 3-methyl-2-butenyl, 3-hexenyl, 7-octenyl, and geranyl. Those having 1 to 6 carbon atoms, especially allyl, are preferred.

The cycloaliphatic group having 3 to 8 carbon atoms may be saturated or unsaturated, and includes, for example, cyclopropyl, cyclopentyl, cyclohexyl, cycloheptyl, cyclooctyl, cyclopentenyl, and cyclohexenyl. Those having 5 or 6 carbon atoms, especially cyclopentyl and cyclohexyl are preferred.

Examples of the phenylalkyl groups include benzyl, phenethyl and phenylpropyl. Phenyl (C$_{1-2}$)alkyl groups such as benzyl and x-phenethyl are preferred.

The acyl group having 2 to 7 carbon atoms includes, for example, acetyl, propionyl, n-butyryl, iso-butyryl, n-valeryl, iso-valeryl, caproyl, enanthyl, and benzoyl. Aliphatic acyl groups having 2 to 6 carbon atoms, such as acetyl, n- or iso-butyryl and caproyl, and a benzoyl group are preferred.

Preferred 5- or 6-membered rings formed by $R^1$ and $R^2$ further contain 1 or 2 nitrogen, oxygen or sulfur atoms. Examples are 1-pyrrolidinyl, 3-thiazolidinyl, piperidino, morpholino and 1-piperazinyl.

The aforesaid $C_{3-8}$ cycloaliphatic groups, phenylalkyl groups and $C_{2-7}$ acyl groups may be substituted. Examples of substituents in these substituted groups and the substituted phenyl groups include halogen atoms such as fluorine, chlorine and bromine; a hydroxyl group; alkyl groups having 1 to 4 carbon atoms which may be substituted by one or more halogen atoms, such as methyl, ethyl, n-propyl, iso-propyl, n-butyl, trifluoromethyl and chloromethyl; alkoxy groups having 1 to 4 carbon atoms which may be substituted by one or more halogen atoms, such as methoxy, ethoxy, n-propoxy, iso-propoxy, n-butoxy, trifluoromethoxy and chloromethoxy; a nitrile group; a carboxyl group; and alkoxycarbonyl groups having 2 to 7 carbon atoms such as methoxycarbonyl, ethoxycarbonyl, butoxycarbonyl, hexyloxycarbonyl.

Preferably, the enolate derivatives of the thiazolo[3,2-a]pyrimidines of general formula (I) are represented by (I)-a wherein $R^1$ and $R^2$ are as defined with regard to formula (I), and $R^3$ is identical with, or different from, $R^1$ or $R^2$, and represents an alkyl group having 1 to 10 carbon atoms, an alkenyl group having 3 to 10 carbon atoms, a substituted or unsubstituted cycloaliphatic group having 3 to 8 carbon atoms, a substituted or unsubstituted phenylalkyl group, a substituted or unsubstituted acyl group having 2 to 7 carbon atoms, or an alkali metal, provided that $R^1$ and $R^2$ are not simultaneously hydrogen atoms or substituted or unsubstituted acyl groups having 2 to 7 carbon atoms; or (I)-b wherein $R^1$ and $R^2$ are as defined with regard to formula (I), and $R^3$ is as defined with regard to formula (I)-a.

Sodium and potassium are preferred examples of the alkali metal represented by $R^3$ *in formulae (I)-a and (I)-b*.

The acid addition salts of the thiazolo[3,2-a]-pyridines of formula (I) or their enolate derivatives in accordance with this invention may be salts with inorganic acids, organic carboxylic acids or organic sulfonic acids, preferably inorganic acids, especially preferably mineral acids.

Examples of the acids include mineral acids such as hydrochloric acid, hydrobromic acid, sulfuric acid and phosphoric acid; organic carboxylic acids such as acetic acid, propionic acid, oxalic acid, citric acid, mandelic acid, maleic acid, fumaric acid, lactic acid and glutamic acid; and organic sulfonic acids such as methanesulfonic acid, ethanesulfonic acid, benzenesulfonic acid, p-toluenesulfonic acid and cumylsulfonic acid.

Of these, the mineral acid salts such as hydrochlorides and sulfates are especially preferred.

In should be understood that the acid addition salts of the enolate derivatives in accordance with the invention do not include those which return to the dioxo compounds of general formula (I) by reaction with acids during their production, for example acid addition salts of enolate derivatives of formulae (I)-a and (I)-b in which $R^3$ is an alkali metal atom.

Examples of the compound of general formula (I) provided by this invention are thiazolo[3,2-a]pyrimidines listed below.

(100) 5H-2,3,6,7-tetrahydro-6-methylamino-5,7-dioxothiazolo[3,2-a]pyrimidine, (102) 6-ethylamino-5H-2,3,6,7-tetrahydro-5,7-dioxothiazolo[3,2-a]pyrimidine, (104) 6-n-hexylamino-5H-2,3,6,7-tetrahydro-5,7-dioxothiazolo[3,2-a]pyrimidine, (106) 6-allylamino-5H-2,3,6,7-tetrahydro-5,7-dioxothiazolo[3,2-a]pyrimidine, (108) 6-(3-hexenylamino)-5H-2,3,6,7-tetrahydro-5,7-dioxothiazolo[3,2-a]pyrimidine,
(110) 6-anilino-5H-2,3,6,7-tetrahydro-5,7-dioxothiazolo[3,2-a]pyrimidine,
(112) 6-p-chloroanilino-5H-2,3,6,7-tetrahydro-5,7-dioxothiazolo[3,2-a]pyrimidine,
(114) 6-o-chloroanilino-5H-2,3,6,7-tetrahydro-5,7-dioxothiazolo[3,2-a]pyrimidine,
(116) 6-m-chloroanilino-5H-2,3,6,7-tetrahydro-5,7-dioxothiazolo[3,2-a]pyrimidine,
(118) 5H-2,3,6,7-tetrahydro-6-p-hydroxyphenylamino5,7-dioxothiazolo[3,2-a]pyrimidine,
(120) 5H-2,3,6,7-tetrahydro-5,7-dioxo-6-p-tolylaminothiazolo[3,2-a]pyrimidine,
(122) 6-p-trifluoromethylphenylamino-5H-2,3,6,7-tetrahydro-5,7-dioxothiazolo[3,2-a]pyrimidine,
(124) 5H-2,3,6,7-tetrahydro-6-p-methoxyphenylamino5,7-dioxothiazolo[3,2-a]pyrimidine,
(126) 6-p-trifluoromethoxyphenylamino-5H-2,3,6,7tetrahydro-5,7-dioxothiazolo[3,2-a]pyrimidine,
(128) 6-p-cyanophenylamino-5H-2,3,6,7-tetrahydro-5,7-dioxothiazolo[3,2-a]pyrimidine,
(130) 6-p-carboxyphenylamino-5H-2,3,6,7-tetrahydro5,7-dioxothiazolo[3,2-a]pyrimidine,
(132) 6-p-ethoxycarbonylphenylamino-5H-2,3,6,7-tetrahydro-5,7-dioxothiazolo[3,2-a]pyrimidine,
(134) 6-cyclopentylamino-5H-2,3,6,7-tetrahydro-5,7-dioxothiazolo[3,2-a]pyrimidine,
(136) 6-cyclohexylamino-5H-2,3,6,7-tetrahydro-5,7-dioxothiazolo[3,2-a]pyrimidine,
(138) 6-benzylamino-5H-2,3,6,7-tetrahydro-5,7-dioxothiazolo[3,2-a]pyrimidine,
(140) 6-p-chlorobenzylamino-5H-2,3,6,7-tetrahydro-5,7-dioxothiazolo[3,2-a]pyrimidine,
(142) 5H-2,3,6,7-tetrahydro-5,7-dioxo-6-α-phenethyl-thiazolo[3,2-a]pyrimidine,
(144) 6-acetamide-5H-2,3,6,7-tetrahydro-5,7-dioxothiazolo[3,2-a]pyrimidine,
(146) 6-n-butyrylamino-5H-2,3,6,7-tetrahydro-5,7-dioxothiazolo[3,2-a]pyrimidine,
(148) 6-caproylamino-5H-2,3,6,7-tetrahydro-5,7-dioxothiazolo[3,2-a]pyrimidine,
(150) 6-benzoylamino-5H-2,3,6,7-tetrahydro-5,7-dioxothiazolo[3,2-a]pyrimidine,
(152) 6-p-chlorobenzoylamino-5H-2,3,6,7-tetrahydro-5,7-dioxothiazolo[3,2-a]pyrimidine,
(160) 5H-2,3,6,7-tetrahydro-6-dimethylamino-5,7-dioxothiazolo[3,2-a]pyrimidine,
(161) 6-diethylamino-5H-2,3,6,7-tetrahydro-5,7-dioxothiazolo[3,2-a]pyrimidine,
(162) 5H-2,3,6,7-tetrahydro-5,7-dioxo-6-dipropylaminothiazolo[3,2-a]pyrimidine,
(164) 5H-2,3,6,7-tetrahydro-6-(N-methylanilino)-5,7-dioxothiazolo[3,2-a]pyrimidine,
(166) 6-(p-chloro-N-methylanilino)-5H-2,3,6,7-tetrahydro-5,7-dioxothiazolo[3,2-a]pyrimidine,
(168) 6-(N-cyclohexyl-N-methylamino)-5H-2,3,6,7-tetrahydro-5,7-dioxothiazolo[3,2-a]pyrimidine,
(170) 6-benzylmethylamino-5H-2,3,6,7-tetrahydro-5,7-dioxothiazolo[3,2-a]pyrimidine,
(172) 6-benzoylmethylamino-5H-2,3,6,7-tetrahydro-5,7-dioxothiazolo[3,2-a]pyrimidine,
(174) 6-(N-allylanilino)-5H-2,3,6,7-tetrahydro-5,7-dioxothiazolo[3,2-a]pyrimidine,
(176) 6-(N-benzyl-N-phenylamino)-5H-2,3,6,7-tetrahydro-5,7-dioxothiazolo[3,2-a]pyrimidine,
(178) 6-(N-benzoyl-N-phenylamino)-5H-2,3,6,7-tetrahydro-5,7-dioxothiazolo[3,2-a]pyrimidine,
(180) 6-dicyclohexylamino-5H-b 2,3,6,7-tetrahydro-5,7-dioxothiazolo[3,2-a]pyrimidine,
(182) 6-dibenzylamino-5H-2,3,6,7-tetrahydro-5,7-dioxothiazolo[3,2-a]pyrimidine,
(184) 5H-2,3,6,7-tetrahydro-5,7-dioxo-6-(1-pyrrolidyl)-thiazolo[3,2-a]pyrimidine,
(186) 5H-2,3,6,7-tetrahydro-5,7-dioxo-6-(3-thiazolyl)-thiazolo[3,2-a]pyrimidine,
(188) 5H-2,3,6,7-tetrahydro-5,7-dioxo-6-piperidinothiazolo[3,2-a]pyrimidine,
(190) 5H-2,3,6,7-tetrahydro-6-morpholino-5,7-dioxothiazolo[3,2-a]pyrimidine,
(192) 5H-2,3,6,7-tetrahydro-5,7-dioxo-6-piperazinylthiazolo[3,2-a]pyrimidine,
(193) 6-p-chloroanilino-5H-2,3,6,7-tetrahydro-5,7-dioxothiazolo[3,2-a]pyrimidine hydrochloride,
(194) 6-p-chloroanilino-5H-2,3,6,7-tetrahydro-5,7-dioxothiazolo[3,2-a]pyrimidine sulfate, and
(195) 6-anilino-5H-2,3,6,7-tetrahydro-5,7-dioxothiazolo[3,2-a]pyrimidine hydrochloride.

It should be understood that the thiazolo[3,2-a]pyrimidines of general formula [I] in accordance with this invention also embrace tautomers, i.e. enol tautomers, based on the oxo group at the 5- or 7-position.

Examples of the enolate derivatives of formula (I)-a provided by this invention are listed below.
(200) 5H-2,3-dihydro-7-methoxy-6-dimethylamino-5-oxothiazolo[3,2-a]pyrimidine,
(202) 5H-2,3-dihydro-7-methoxy-5-oxo-6-di-n-propylaminothiazolo[3,2-a]pyrimidine,
(204) 6-anilino-5H-2,3-dihydro-7-methoxy-5-oxothiazolo[3,2-a]pyrimidine,
(206) 6-p-chloroanilino-5H-2,3-dihydro-7-methoxy-5-oxothiazolo[3,2-a]pyrimidine,
(208) 5H-2,3-dihydro-7-methoxy-6-(N-methylanilino)-5-oxothiazolo[3,2-a]pyrimidine,
(210) 5H-2,3-dihydro-7-methoxy-6-(p-chloro-N-methylanilino)-oxothiazolo[3,2-a]pyrimidine,
(212) 7-n-butoxy-6-(N-n-butylanilino)-5H-2,3-dihydro-5-oxothiazolo[3,2-a]pyrimidine,
(214) 6-anilino-7-n-butoxy-5H-2,3-dihydro-5-oxothiazolo[3,2-a]pyrimidine,
(216) 6-benzylamino-5H-2,3-dihydro-7-methoxy-5-oxothiazolo[3,2-a]pyrimidine,
(218) 6-(N-benzyl-N-methylamino)-5H-2,3-dihydro-7-methoxy-5-oxothiazolo[3,2-a]pyrimidine,
(220) 6-(N-allylanilino)-7-ethoxy-5H-2,3-dihydro-5-oxothiazolo[3,2-a]pyrimidine,
(222) 6-(N-cyclohexyl-N-methylanimo)-5H-2,3-dihydro-7-methoxy-5-oxothiazolo[3,2-a]pyrimidine,
(224) 6-(N-benzoyl-N-phenylamino)-5H-2,3-dihydro-7-methoxy-5-oxothiazolo[3,2-a]pyrimidine,
(226) 7-ethoxy-5H-2,3-dihydro-5-oxo-6-piperidinothiazolo[3,2-a]pyrimidine,
(230) 7-allyloxy-5H-2,3-dihydro-5-oxo-6-di-n-propylthiazolo[3,2-a]pyrimidine,
(232) 6-(N-allylanilino)-7-allyloxy-5H-2,3-dihydro-5-oxothiazolo[3,2-a]pyrimidine,
(234) 7-allyloxy-6-anilino-5H-2,3-dihydro-5-oxothiazolo[3,2-a]pyrimidine,
(236) 7-allyloxy-6-(N-cyclohexyl-N-methylamino)-5H-2,3-dihydro-5-oxothiazolo[3,2-a]pyrimidine,
(238) 7-allyloxy-6-(N-benzoyl-N-phenylamino)-5H-2,3-dihydro-5-oxothiazolo[3,2-a]pyrimidine,
(240) 7-allyloxy-5H-2,3-dihydro-6-morpholino-5-oxothiazolo[3,2-a]pyrimidine,
(242) 7-(3-hexenyloxy)-5H-2,3-dihydro-6-dimethylamino-5-oxothiazolo[3,2-a]pyrimidine, (250) 7-benzyloxy-6-diethylamino-5H-2,3-dihydro-5-oxothiazolo[3,2-a]pyrimidine,
(252) 6-(N-allyl-N-phenylamino)-7-benzyloxy-5H-2,3-dihydro-5-oxothiazolo[3,2-a]pyrimidine,
(256) 7-benzyloxy-6-(N-cyclohexyl-N-methylamino)-5H-2,3-dihydro-5-oxothiazolo[3,2-a]pyrimidine,
(258) 6-anilino-7-benzyloxy-5H-2,3-dihydro-5-oxothiazolo[3,2-a]pyrimidine,
(260) 7-benzyloxy-6-(N-benzyl-N-phenylamino)-5H-2,3-dihydro-5-oxothiazolo[3,2-a]pyrimidine,
(262) 6-benzylamino-7benzyloxy-5H-2,3-dihydro-5-oxothiazolo[3,2-a]pyrimidine,
(264) 6-(N-benzoyl-N-phenylamino)-7-benzyloxy-5H-2,3-dihydro-5-oxothiazolo[3,2-a]pyrimidine,
(266) 5H-2,3-dihydro-5-oxo-7-α-phenethyloxy-6-(2-piperazinyl)thiazolo[3,2-a]pyrimidine,
(267) 6-(N-cyclohexyl-N-methylamino)-5H-2,3-dihydro-7-hydroxy-5-oxothiazolo[3,2-a]pyrimidine sodium salt,
(268) 5H-2,3-dihydro-7-hydroxy-5-oxo-6-di-n-propylaminothiazolo[3,2-a]pyrimidine sodium salt,
(269) 6-p-chloroanilino-5H-2,3-dihydro-7-hydroxy-5-oxothiazolo[3,2-a]pyrimidine sodium salt,
(270) 7-acetoxy-5H-2,3-dihydro-5-oxo-6-di-n-propylaminothiazolo[3,2-a]pyrimidine,
(272) 7-acetoxy-6-(N-acetyl-N-methylamino)-5H-2,3-dihydro-5-oxothiazolo[3,2-a]pyrimidine,
(274) 7-acetoxy-6-(N-allyl-N-phenylamino)-5H-2,3-dihydro-5-oxothiazolo[3,2-a]pyrimidine,
(276) 7-acetoxy-6-(N-cyclohexyl-N-methylamino)-5H-2,3-dihydro-5-oxothiazolo[3,2-a]pyrimidine,
(278) 7-acetoxy-6-(N-acetyl-N-phenylamino)-5H-2,3-dihydro-5-oxothiazolo[3,2-a]pyrimidine,
(280) 7-acetoxy-5H-2,3-dihydro-6-(N-methylanilino)-5-oxothiazolo[3,2-a]pyrimidine,
(282) 7-acetoxy-6-(N-benzyl-N-methylamino)-5H-2,3-dihydro-5-oxothiazolo[3,2-a]pyrimidine,
(284) 7-acetoxy-5H-2,3-dihydro-5-oxo-6-(3-thiazolidinyl)thiazolo[3,2-a]pyrimidine,
(286) 7-benzoyloxy-5H-2,3-dihydro-6-dimethylamino-5-oxothiazolo[3,2-a]pyrimidine,
(288) 6-(N-allyl-N-phenylamino)-7-benzoyloxy-5H-2,3-dihydro-5-oxothiazolo[3,2-a]pyrimidine,
(290) 7-benzoyloxy-6-(N-cyclohexyl-N-methylamino)-5H-2,3-dihydro-5-oxothiazolo[3,2-a]pyrimidine,
(292) 7-benzoyloxy-5H-2,3-dihydro-6-(N-methylanilino)-5-oxothiazolo[3,2-a]pyrimidine,
(294) 7-benzoyloxy-6-(N-benzyl-N-methylamino)-5H-2,3-dihydro-5-oxothiazolo[3,2-a]pyrimidine,
(296) 7-benzoyloxy-5H-2,3-dihydro-5-oxo-6-(1-pyrrolidinyl)-thiazolo[3,2-a]pyrimidine,
(298) 7-cyclohexyloxy-5H-2,3-dihydro-6-(N-methylanilino)-5-oxothiazolo[3,2-a]pyrimidine, and
(299) 6-anilino-5H-2,3-dihydro-7-hydroxy-5-oxothiazolo[3,2-a]pyrimidine sodium salt.

Examples of the enolate derivatives of formula (I)-b provided by this invention are listed below.
(300) 5H-2,3-dihydro-5-methoxy-6-dimethylamino-7-oxothiazolo[3,2-a]pyrimidine,
(302) 6-anilino-5H-2,3-dihydro-5-methoxy-7-oxothiazolo[3,2-a]pyrimidine,
(304) 5H-2,3-dihydro-5-methoxy-6-(N-methylanilino)-7-oxothiazolo[3,2-a]pyrimidine,
(306) 6-(p-chloro-N-methylanilino)-5H-2,3-dihydro-5-methoxy-7-oxothiazolo[3,2-a]pyrimidine,
(308) 6-benzylamino-5H-2,3-dihydro-5-methoxy-7-oxothiazolo[3,2-a]pyrimidine,
(310) 5-allyloxy-5H-2,3-dihydro-7-oxo-6-di-n-propylthiazolo[3,2-a]pyrimidine,
(312) 5-benzyloxy-6-diethylamino-5H-2,3-dihydro-7-oxothiazolo[3,2-a]pyrimidine,
(314) 6-anilino-5-benzyloxy-5H-2,3-dihydro-7-oxothiazolo[3,2-a]pyrimidine,
(316) 5-acetoxy-6-(N-acetyl-N-methylamino)-5H-2,3-dihydro-7-oxothiazolo[3,2-a]pyrimidine,
(318) 5-acetoxy-5H-2,3-dihydro-6-(N-methylanilino)-7-oxothiazolo[3,2-a]pyrimidine,
(320) 5-benzoyloxy-5H-2,3-dihydro-6-dimethylamino-7-oxothiazolo[3,2-a]pyrimidine,
(322) 5-benzoyloxy-5H-2,3-dihydro-6-(N-methylanilino)-7-oxothiazolo[3,2-a]pyrimidine, and
(324) 5-benzoyloxy-5H-2,3-dihydro-7-oxo-6-(1-pyrrolidinyl)-thiazolo[3,2-a]pyrimidine.

According to this invention, the thiazolo[3,2-a]pyrimidines of general formula (I) can be produced by (a) reacting a malonic acid derivative of the following general formula

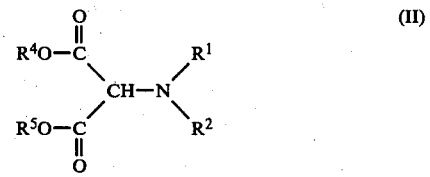

wherein $R^1$ and $R^2$ are as defined with regard to formula (I), and $R^4$ and $R^5$ are identical or different and each represents an alkyl group having 1 to 6 carbon atoms, with 2-aminothiazoline under heat, if desired in the presence of an inert organic solvent, to induce cyclocondensation, or (b) performing said condensation reaction in the presence of an alkali metal alkoxide, if desired in the presence of an inert organic solvent, and neutralizing the resulting enolate with an acid; and as required, reacting the reaction product of (a) or (b) with an acid.

Examples of the alkyl group having 1 to 6 carbon atoms for $R^4$ and $R^5$ in formula (II) are methyl, ethyl, n-propyl, iso-propyl, n-butyl, iso-butyl, sec-butyl, tert-butyl, n-pentyl and n-hexyl. Those having 1 to 5 carbon atoms, especially methyl and ethyl are preferred, and above all, $R^4$ and $R^5$ are preferably both methyl or ethyl.

Examples of the malonic acid derivative of formula (II) include di-$C_{1-6}$ alkyl esters, preferably dimethyl or diethyl esters, of N-methylaminomalinic acid, N-ethylaminomalonic acid, N-n-hexylaminomalonic acid, N-allylaminomalonic acid, N-3-hexenylaminomalonic acid, anilinomalonic acid, p-chloroanilinomalonic acid, o-chloroanilinomalonic acid, m-chloroanilinomalonic acid, p-hydroxyphenylaminomalonic acid, p-tolylaminomalonic acid, p-trifluoromethylphenylaminomalonic acid, p-methoxyphenylaminomalonic acid, p-trifluoromethoxyphenylaminomalonic acid, p-cyanophenylaminomalonic acid, p-ethoxyphenylaminomalonic acid, N-cyclopentylaminomalonic acid, N-cyclohexylaminomalonic acid, N-benzylaminomalonic acid, N-p-chlorobenzylaminomalonic acid, N-α-phenethylaminomalonic acid, N-dimethylaminomalonic acid, N-diethylaminomalonic acid, N-di-n-propylaminomalonic acid, N-methylanilinomalonic acid, p-chloro-N-methylanilinomalonic acid, N-cyclohexyl-N-methylaminomalonic acid, N-benzyl-N- methylaminomalonic acid, N-allylaminomalonic acid, N-benzyl-N-phenylaminomalonic acid, N-dicyclohexylaminomalonic acid, N-dibenzylaminomalonic acid, 1-pyrrolidylmalonic acid, 3-thiazolylmalonic acid, piperidylmalonic acid, morpholinomalonic acid and piperazinomalonic acid.

Such malonic acid derivatives of formula (II) can be produced by reacting under heat the corresponding halo-malonic acid diesters, preferably bromomalonic acid diesters or chloromalonic acid diesters, with the corresponding amines in an inert organic solvent such as benzene, toluene and xylene, preferably in the presence of an excess of the aforesaid amines or tertiary amines. The manufacturing method is described, for example, in J. Org. Chem., vol. 20, pages 1454–1457 (1955).

The other starting material is 2-aminothiazoline of the following formula:

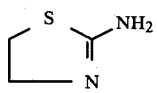

The process of the invention is carried out by subjecting the malonic acid derivative (II) and 2-aminothiazoline to cyclocondensation. The cyclocondensation is a reaction of equimolar proportions of the malonic acid derivative and 2-aminothiazoline. According to the process of this invention, 0.8 to 1.2 moles of 2-aminothiazoline is preferably used per mole of the malonic acid derivative.

The cyclocondensation reaction may be carried out (a) under heat or (b) in the presence of an alkali metal alkoxide, if desired in the presence of an inert organic solvent. Preferably, it is carried out under heat. When it is carried out in the presence of an alkali metal alkoxide, the reaction product is obtained as an enolate of the alkali metal, and therefore, the product should subsequently be neutralized with an acid.

The cyclocondensation reaction under heat is preferably carried out in the presence of an inert organic solvent. Advantageously, the inert organic solvent is an aprotic inert organic solvent. Examples of such inert organic solvents are aprotic inert organic solvents such as toluene, xylene, cumene, cymene, tetralin, decalin, diethylene glycol dimethyl ether, diethylene glycol diethyl ether, diethylene glycol dibutyl ether, diphenyl ether, dimethyl sulfoxide, dimethyl formamide and nitrobenzene; and lower alcohols having 1 to 4 carbon atoms such as ethanol and butanol.

The amount of the inert organic solvent used is about 1 to about 50 parts by weight, preferably about 2 to about 20 parts by weight, per part by weight of the malonic acid derivative (II) and 2-aminothiazoline combined.

The reaction temperature and time differ depending upon the types of the starting materials, the presence or absence of the solvent, and the type of the solvent used. Usually, the reaction is carried out at 80° to 320° C. for 1 minute to 48 hours, preferably at 100° to 300° C. for 1 minute to 48 hours, preferably at 100° to 300° C. for 10 minutes to 24 hours. The reaction can be performed at atmospheric or elevated pressures.

When a lower alcohol is used as the reaction solvent, the reaction is preferably carried out at an elevated pressure in order to increase the reaction temperature.

The reaction product formed by the cyclocondensation reaction in the above manner is a thiazolo[3,2-a]pyrimidine of formula (I).

Isolation of the reaction product from the reaction mixture and its purification can be easily performed by usual methods such as recrystallization, chromatography and extraction.

In the presence of an alkali metal alkoxide as a catalyst, the cyclocondensation reaction can be carried out at a relatively low temperature. Preferred alkali metal alkoxides are $C_{1-4}$ alkoxides of lithium, sodium or potassium. Examples of the alkali metal alkoxide used in the invention are lithium methoxide, lithium ethoxide, lithium propoxide, sodium methoxide, sodium ethoxide, sodium propoxide, sodium iso-propoxide, sodium butoxide, sodium is iso-butoxide, sodium sec-butoxide, sodium t-butoxide, potassium methoxide, potassium ehtoxide, potassium propoxide, potassium iso-propoxide, potassium butoxide, potassium iso-butoxide, potassium sec-butoxide and potassium t-butoxide. Sodium methoxide and sodium ethoxide are preferred.

The amount of the alkali metal alkoxide used is 1 to 10 moles, preferably 1 to 2 moles, per mole of the malonic acid derivative (II) used.

When the cyclocondensation reaction is carried out in the presence of the alkali metal alkoxide, a $C_{1-4}$ alcohol is preferred as the reaction solvent. Examples of the lower alcohol include methanol, ethanol, propanol, iso-propanol, butanol, iso-butanol, sec-butanol and 5-butanol. A mixture of the lower alcohol and another inert organic solvent (e.g., the aprotic inert solvents mentioned above) can also be used as the reaction solvent. The amount of the reaction solvent is usually 1 to 50 parts by weight, preferably 2 to 10 parts by weight, per part by weight of the malonic acid derivative and 2-aminothiazoline combined.

The reaction time and temperature differ depending upon the types of the starting materials the solvent and the alkali metal alkoxide used. Usually, the reaction is carried out at 40° to 150° C. for 30 minutes to 72 hours, preferably at 60° to 120° C. for 1 to 10 hours. The reaction may be carried out at atmospheric to elevated pressures.

A procedure which is preferably taken in actually performing the reaction is to add an alkali metal such as sodium to the lower alcohol to prepare a lower alcohol solution of the alkali metal alkoxide, and then add the malonic acid derivative (II) and 2-aminothiazoline for cyclocondensation.

The reaction product formed by the cyclocondensation reaction in the presence of the alkali metal alkoxide is an enolate of the alkali metal. The enolate is then neutralized with an acid to give the thiazolo[3,2-a]pyrimidine of formula (I).

The neutralization reaction can be effected by adding an amount, required for neutralization, of an acid to the reaction mixture obtained by the cyclocondensation reaction, or by first isolating the enolate from the reaction mixture and then adding the required amount of an acid in water. The acid may be an inorganic acid, organic sulfonic acid or organic carboxylic acid. Preferred are inorganic acids, for example mineral acids such as hydrochloric acid and hydrobromic acid, and organic carboxylic acids such as acetic acid.

The final product obtained is isolated and purified by usual means such as recrystallization, chromatography and extraction.

The thiazolo[3,2-a]pyrimidines of formula (I) obtained by the cyclocondensation reaction through route (a) or (b) may be formed into acid addition salts by addition-reaction with acids. The addition reaction may be performed by using the isolated thiazolo[3,2-a]pyrimidines or the reaction mixture containing the thiazolo[3,2-a]pyrimidines. Or it can be performed simultaneously with the aforesaid neutralization reaction of the enolates.

The enolate derivatives of the thiazolo[3,2-a]pyrimidines of formula (I) can be produced by the following method in accordance with this invention.

The enolate derivatives of formula (I)-a or (I)-b in which $R^3$ is a $C_{1-10}$ alkyl group, a $C_{3-10}$ alkenyl group, a substituted or unsubstituted $C_{3-8}$ cycloaliphatic group or a substituted or unsubstituted phenylalkyl group can be produced by reacting a thiazolo[3,2-a]pyrimidine of the following formula

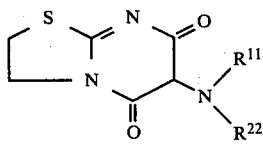
(I)-1 wherein $R^{11}$ and $R^{22}$ are identical or different, and each represents an alkyl group having 1 to 10 carbon atoms, an alkenyl group having 3 to 10 carbon atoms, a substituted or unsubstituted phenyl group, a substituted or unsubstituted cycloaliphatic group having 3 to 8 carbon atoms, a substituted or unsubstituted phenylalkyl group, or a substituted or unsubstituted acyl group having 2 to 7 carbon atoms provided that $R^{11}$ and $R^{22}$ are not simultaneously substituted or unsubstituted acyl groups having 2 to 7 carbon atoms; and $R^{11}$ and $R^{22}$, may form, taken together with the nitrogen atom to which they are bonded, a 5- or 6-membered ring which may further contain one or more hetero atoms with a halogen compound of the following formula $R^6$—X (III)

wherein X represents a halogen atom, and $R^6$ represents an alkyl group having 1 to 10 carbon atoms, an alkenyl group having 3 to 10 carbon atoms, a substituted or unsubstituted cycloaliphatic group having 3 to 8 carbon atoms, or a substituted or unsubstituted phenylalkyl group,
in a polar organic solvent in the presence of a basic compound, and if desired, reacting the resulting product with an acid.

The thiazolo[3,2-a]pyrimidines of formula (I)-1 are compounds which are embraced within the general formula (I) [compounds of formula (I) in which both of $R^1$ and $R^2$ are other than hydrogen atoms in the definition given hereinabove].

$R^6$ in formula (III) represents an alkyl group having 1 to 10 carbon atoms, an alkenyl group having 3 to 10 carbon atoms, a substituted or unsubstituted cycloaliphatic group having 3 to 8 carbon atoms, or a substituted or unsubstituted phenyl alkyl group.

Examples of those various groups represented by $R^6$ in formula (III) may be the same as those given hereinabove with regard to formula (I). Examples of X for $R^6$ are chlorine, bromine and iodine.

Examples of the halogen compound of formula (III) include methyl chloride, methyl bromide, methyl iodide, ethyl bromide, ethyl iodide, n-propyl bromide, iso-propyl bromide, n-butyl bromide, sec-butyl bromide, n-pentyl bromide, iso-pentyl bromide, n-hexyl bromide, n-decyl bromide, allyl bromide, 3-hexenyl chloride, cyclohexyl bromide, 4-methylcyclohexyl bromide, benzyl chloride, benzyl bromide, benzyl iodide, and p-chlorobenzyl bromide.

Stoichiometrically, the thiazolo[3,2-a]pyrimidine of formula (I)-1 and the halogen compound of formula (III) react in equimolar proportions. Usually, it is desirable to use about 1 to about 10 moles of the halogen compound (III) per mole of the thiazolo[3,2-a]pyrimidine. The unreacted halogen compound (III) may be recovered after the reaction for re-use.

The reaction is carried out in the presence of a basic compound in an inert organic solvent.

Examples of the basic compound used in the reaction include sodium hydride; sodium amide; alkali or alkaline earth metal hydroxides, bicarbonates or carbonates such as sodium hydroxide, potassium hydroxide, sodium carbonate, potassium carbonate, sodium hydrogen carbonate, potassium hydrogen carbonate, calcium hydroxide and calcium carbonate; metal alkoxides such as sodium methoxide, sodium ethoxide, potassium methoxide, potassium ethoxide, sodium isopropoxide, potassium isopropoxide and potassium t-butoxide; and organic bases such as trimethylamine, triethylamine, diethylamine, diisopropylamine, pyridine, lutidine, collidine and imidazole. Sodium hydride, pyridine and triethylamine are preferred.

The amount of the basic compound used is usually about 1 to 3 moles, preferably 1.1 to 2 moles, per mole of the thiazolo[3,2-a]pyrimidine used.

Examples of the inert organic solvent are protic or aprotic polar solvents such as methanol, ethanol, dimethyl sulfoxide, dimethyl formamide and pyridine, and aprotic solvents such as methylene chloride, chloroform, benzene, toluene, xylene, diethyl ether and tetrahydrofuran.

The amount of the organic solvent is about 1 to about 50 parts by weight, preferably about 2 to about 20 parts by weight, per part by weight of the starting materials and the basic compound combined.

The reaction is carried out usually at about 10° to about 100° C., preferably at about 15° to about 50° C. Usually, the reaction comes to completion in about 1 to about 72 hours. The reaction can be carried out at atmospheric to elevated pressures, preferably under atmospheric pressure.

The above reaction thus gives enolate derivatives of the following formula

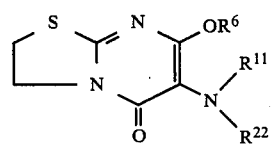
(I)-a₁ and/or the following formula

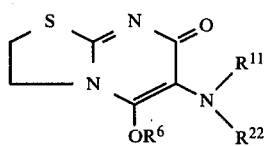 (I)-b₁ wherein $R^6$, $R^{11}$ and $R^{22}$ are as defined hereinabove. Usually, a mixture of the enolate derivatives of formulae (I)-a₁ and (I)-b₁ results.

The enolate derivative so obtained is isolated and purified, either as a mixture or as the individual components, by recrystallization, chromatography (e.g., column chromatography), extraction, etc.

The enolate derivatives may be converted to their acid addition salts by the method already described hereinabove.

Those enolate derivatives of formula (I)-a and (I)-b in which $R^3$ is a substituted or unsubstituted acyl group having 2 to 7 carbon atoms can be produced by reacting the thiazolo[3,2-a]pyrimidines of formula (I)-1 with acid halides or acid anhydrides of carboxylic acids of the following formula $$R^7-OH \qquad (IV)$$

wherein $R^7$ is a substituted or unsubstituted acyl group having 2 to 7 carbon atoms,
in an aprotic inert organic solvent, if desired in the presence of a basic compound, and as required, reacting the resulting product with an acid.

Examples of the acyl group for $R^7$ are the same as those given hereinabove with regard to formula (I).

Examples of the carboxylic acid expressed by general formula (IV) include acetic acid, propionic acid, butyric acid, isobutyric acid, n-valeric acid, iso-valeric acid, caproic acid, enanthic acid, benzoic acid, trifluoroacetic acid and p-chlorobenzoic acid. In the process of this invention, the carboxylic acid is used as its reactive derivative, i.e. an acid halide such as an acid chloride or acid bromide, or as an acid anhydride.

Stoichiometrically, the thiazolo[3,2-a]pyrimidine of formula (I)-1 and the acid halide or anhydride react in equimolar proportions. Usually, the amount of the acid halide or anhydride is used is about 1 to about 3 moles, preferably about 1.1 to about 2 moles, per mole of the thiazolo[3,2-a]pyrimidine.

The reaction is carried out in an aprotic inert organic solvent, if desired in the presence of a basic compound.

Examples of the aprotic inert organic solvent are methylene chloride, chloroform, dichloroethane, carbon tetrachloride, chlorobenzene, benzene, toluene, xylene, diethyl ether, tetrahydrofuran, dimethyl formamide, and dimethyl acetamide.

The basic compound may be the same as those exemplified hereinabove.

The amounts of the aprotic inert organic solvent and the basic compound may be the same as those described hereinabove.

The reaction is carried out usually at about 0° C. to about 100° C., preferably about 5° C. to about 50° C. The reaction is usually carried out under atmospheric pressure. The reaction usually comes to completion in several minutes to about 12 hours.

The above reaction thus provides enolate derivatives of the formula

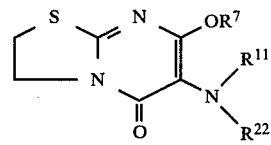 (I)-a₂ and/or the following formula

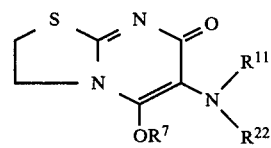 (I)-b₂ wherein $R^7$, $R^{11}$ and $R^{22}$ are as defined hereinabove.

The enolate derivatives represented by the above formulae (I)-a₂ and (I)-b₂ can be separated and purified as a mixture or as the individual components, or converted into acid addition salts, by the same methods as described hereinabove.

According to the invention, the enolate derivatives of formulae (I)-a₁ and (I)-b₁ can also be produced by reacting a thiazolo[3,2-a]pyrimidine of the following formula

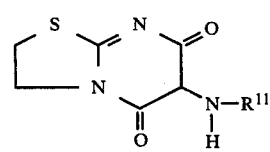 (I)-2 wherein $R^{11}$ is as defined with regard to the above formula (I)-a₁,
with the halogen compound of formula (III) above in a polar organic solvent in the presence of a basic compound, and then as required, reacting the resulting product with an acid.

The halogen compound, basic compound and polar solvent used in this reaction and the reaction conditions may be quite the same as those used in the aforesaid process for producing the enolate derivatives of formula (I)-a₁ and/or (I)-b₁.

This reaction can also afford enolate derivatives corresponding to general formula (I)-a and (I)-b in which $R^2$ is a hydrogen atom.

In other words, according to the above reaction, there can be produced enolate derivatives of thiazolo[3,2-a]pyrimidines of the following general formula

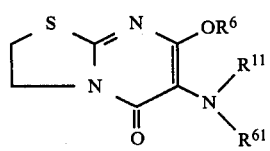 (I)-a₃ and/or the following general formula

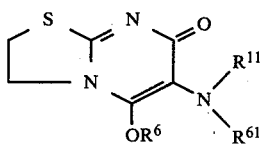 (I)-b3 wherein $R^6$ and $R^{11}$ are as defined with regard to formula (I)-a₁ and $R^{61}$ is a hydrogen atom or the same as $R^6$; and their acid addition salts.

According to this invention, the enolate derivatives of general formulae (I)-a₂ and (I)-b₂ can also be produced by reacting the thiazolo[3,2-a]pyrimidine of formula (I)-2 with an acid halide or anhydride of the carboxylic acid of formula (IV) in an aprotic inert organic solvent in the optional presence of a basic compound, and as required, reacting the reaction product with an acid.

The acid halide or anhydride, aprotic inert organic solvent and basic compound used in this reaction and the reaction conditions may be quite the same as those used in the aforesaid process for producing the enolate derivatives of general formula (I)-a₂ and/or general formula (I)-b₂.

The above reaction can afford compounds corresponding to general formula (I)-a in which $R^2$ is a hydrogen atom, and/or compounds corresponding to general formula (I) in which $R^2$ is a substituted or unsubstituted acyl group having 2 to 7 carbon atoms. In other words, the above reaction gives thiazolo[3,2-a]pyrimidines and/or their enolate derivatives, which are represented by the following general formula

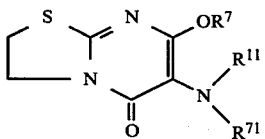 (I)-a4 and/or the following general formula

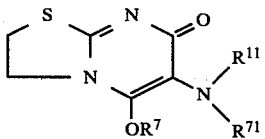 (I)-b4 and/or the following general formula

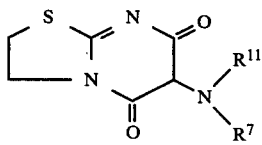 (I)-1 wherein $R^7$ and $R^{11}$ are as defined with regard to formula (I)-a₂, and $R^{71}$ is a hydrogen atom or the same as $R^7$.

The above-described processes of the invention give the thiazolo[3,2-a]pyrimidines or the enolate derivatives thereof, or the acid addition salts of these which are claimed in this invention.

Investigations of the present inventors have also shown that those enolate derivatives provided by the invention which correspond to the above general formula (I)-a can further be converted to their S-oxides. Accordingly, the present invention also provides S-oxides of the enolate derivatives of thiazolo[3,2-a]pyrimidines, which are represented by the following general formula

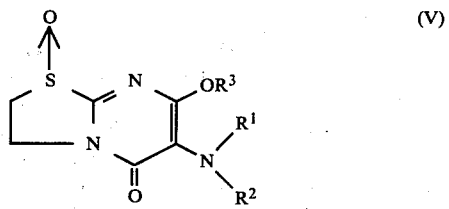 (V)

wherein $R^1$, $R^2$ and $R^3$ are as defined with regard to formula (I)-a.

Specific examples of these S-oxides include the following.

(400) 5H-2,3-dihydro-7-methoxy-6-dimethylamino-5-oxothiazolo[3,2-a]pyrimidine-1-oxide,
(402) 5H-2,3-dihydro-7-methoxy-5-oxo-6-di-n-propyl-aminothiazo[3,2-a]pyrimidine-1-oxide,
(404) 6-anilino-5-H-2,3-dihydro-7-methoxy-5-oxo-thiazolo[3,2-a]pyrimidine-1-oxide,
(406) 6-p-chloroanilino-5H-2,3-dihydro-7-methoxy-5-oxothiazolo[3,2-a]pyrimidine-1-oxide,
(408) 6-(p-chloro-N-methylanilino)-5H-2,3-dihydro-7-methoxy-5-oxothiazolo[3,2-a]pyrimidine-1-oxide,
(410) 6-anilino-7-n-butoxy-5H-2,3-dihydro-5-oxo-thiazolo[3,2-a]pyrimidine-1-oxide,
(412) 6-(N-allylanilino)-7-allyloxy-5H-2,3-dihydro-5-oxothiazolo[3,2-a]pyrimidine-1-oxide,
(414) 7-allyloxy-6-anilino-5-H-2,3-dihydro-5-oxo-thiazolo[3,2-a]pyrimidine-1-oxide,
(416) 6-anilino-7-benzyloxy-5H-2,3-dihydro-5-oxo-thiazolo[3,2-a]pyrimidine-1-oxide,
(418) 7-benzyloxy-6-(N-benzyl-N-phenylamino)-5H-2,3-dihydro-5-oxothiazolo[3,2-a]pyrimidine-1-oxide,
(420) 7-acetoxy-6-(N-acetyl-N-methylamino)-5H-2,3-dihydro-5-oxothiazolo[3,2-a]pyrimidine-1-oxide,
(422) 7-acetoxy-6-(N-acetoxy-N-phyenylamino)-5H-2,3-dihydro-5-oxothiazolo[3,2-a]pyrimidine-1-oxide,
(424) 7-benzolyloxy-5H-2,3-dihydro-6-dimethylamino-5-oxothiazolo[3,2-a]pyrimidine-1-oxide,
(426) 6-(N-allyl-N-phenylamino)-7-benzoyloxy-5H-2,3-dihydro-5-oxothiazolo[3,2-a]pyrimidine-1-oxide,
(428) 7-benzoyloxy-5H-2,3-dihydro-5-oxo-6-(1-pyrrolidinyl)-thiazolo[2,3-a]pyrimidine-1-oxide, and
(430) 5H-2,3-dihydro-7-methoxy-6-(N-methylanilino)-5-oxothiazolo[3,2-a]pyrimidine-1-oxide.

These S-oxides can be produced by oxidizing the enolate derivatives of formula (I)-a with an oxidizing agent in an inert organic solvent.

Examples of the oxidizing agents include peracids such as peracetic acid, performic acid, perbenzoic acid and per-m-chlorobenzoic acid; alkyl hydroperoxides such as iso-butyl hydroperoxide, sec-butyl hydroperoxide and, t-butyl hydroperoxide per-acid salts such as sodium perchlorate and sodium periodate; imide compounds such as N-bromosuccinimide and N-chlorosuccinimide; and hydrogen peroxide. The amount of the oxidizing agent used is usually 1 to 100 equivalents, preferably 0.5 to 3 equivalents, per equivalent of the enolate derivative used.

Examples of preferred inert organic solvents used in the above reaction are acetic acid, methylene chloride, chloroform, 1,2-dichloroethane, benzene and ethyl acetate. The amount of the solvent used is usually 1 to 1000 parts by volume preferably 2 to 20 parts by volume, per part by volume of the startng enolate derivative.

The reaction temperature is preferably in the range of from $-78°$ C. to $50°$ C., especially preferably from $-20°$ C. to $30°$ C. The reaction time, which differs depending upon the type of the starting compound, the reaction temperature, and the type of the oxidizing agent, is usually from 30 minutes to 48 hours.

The sulfoxide can be separated from the reaction mixture and purified by usual methods such as column chromatography and recrystallization.

It has been found in accordance with this invention that the thiazolo[3,2-a]pyrimidines of general formula (I), their enol derivatives, and the acid addition salts, especially pharmaceutically acceptable acid addition salts of these compounds show immune potentiating activity both in a test delayed type hypersensitivity and a plaque forming cells test, and are useful as immune regulating agents.

Thus, according to this invention, there is also provided a pharmaceutical composition comprising the thiazolo[3,2-a]pyrimidine of general formula (I) or its enolate derivative or a pharmaceutically acceptable acid addition salt thereof as an active ingredient and a pharmaceutically acceptable carrier or diluent.

According to this invention, the dosage of the active ingredient is about 0.1 to about 50 mg/kg of body weight/day, preferably about 1 to about 10 mg/kg of body weight/day.

The active ingredient in accordance with this invention may be administered singly, but it is convenient to administer it as the aforesaid pharmaceutical composition or as a medicament in unit dosage form.

The active ingredient of the invention can be adminsitered orally parenterally (e.g., intravenously, subcutaneously, intramuscularly), or intrarectally. The oral route is advantageous.

For oral administration, it is formulated into a solid or liquid preparation. Examples of the solid preparation include tablets, pills, powders, granules and sugar-coated tablets. The solid preparation can be formed by intimately mixing the active ingredient of the invention with a diluent such as calcium carbonate, potato starch, alginic acid and lactose and as required, further with a lubricant such as magnesium stearate, and formulating the mixture in a customary manner. Examples of the liquid preparation include emulsions, solutions, suspensions, syrups and elixirs. The liquid preparation can be formed by intimately mixing the active ingredient of the invention with a medium such as water or liquid paraffin and as required, further with a lubricant, a suspending aid, a sweetening, a flavoring agent, or an antispectic, and formulating the mixture in a customary manner.

For intrarectal administration, the active ingredient of the invention is formed as a suppository by intimately mixing it with a carrier normally used for suppository formulation.

For intravenous, subcutaneous and intramuscular administration, the active ingredient of the invention is formulated into a liquid preparation which may be in the form of, for example, a solution, suspension or emulsion in an aseptic aqueous or non-aqueous medium.

Examples of the non-aqueous medium include propylene glycol, polyethylene glycol, vegetable oils such as olive oil, and organic acid esters usable in injection such as ethyl oleate. If required, these liquid preparations may further contain adjuvants such as antiseptics, wetting agents, emulsifiers and dispersants. Sterilization can be effected by filtration through a bacterium-holding filter, or by incorporating a germicide, or by irradiation. Such a liquid preparation can also be formed by first producing an aseptic solid perparation, and dissolving it aseptically in sterilized water sterilized solvent for injection immediately before administration.

The active ingredient in accordance with this invention is administered to warm-blooded animals such as human beings to regulate the immune function of these animals.

For example, the active compounds in accordance with this invention are useful for treating collagen diseases such as rheumatic fever, systemic lupus erythematosus, scleroderma, multiplearteritis and dermatomyositis; cancer; infections; immunodeficiency with proptopathic or crucial infectious diseases or lymphoma or immunodeficiency resulting from steroidal therapy and immune diseases with aging. They can also be used together with antibiotics with drugs which lower immune, for example steroidal agents, anticancerous agents and immunorupressants.

The following Examples illustrate the present invention in greater detail.

EXAMPLE 1

Synthesis of 6-p-chloroanilino-5H-2,3,6,7-tetrahydro-5,7-dioxo-thiazolo[3,2-a]pyrimidine (No. 112):

(1) Synthesis of diethyl p-chloroanilinomalonate p-Chloroaniline (2 g) was dissolved in dry benzene (20 ml), and diethyl bromomalonate (3.8 g) and then dry pyridine (1.3 ml) were added. The mixture was refluxed with stirring overnight. The solvent was distilled off under reduced pressure, and then water was added. The mixture was extracted with chloroform twice. The chloroform layers were washed with water twice and dried over anhydrous sodium sulfate. The solvent was distilled off under reduced pressure. The residue (3.34 g) was purified by silica gel column chromatography using benzene as an eluent to give 1.56 g (yield 35%) of diethyl p-chloroanilinomalonate having the following NMR data.

NMR ($\delta_{TMS}^{CDCl_3}$): 1.26 (6H, t, J=7Hz), 4.28 (4H, q, J=7Hz), 4.6–5.0 (2H, m: 1H when D$_2$O was added), 6.63 (2H, d, J=9Hz), and 7.19 (2H, d, J=9Hz).

(2) Synthesis of compound No. 112

Metallic sodium (120 mg) was added to anhydrous ethanol (3 ml) to prepare a solution of sodium ethoxide in ethanol, and a suspension of the diethyl p-chloroanilinomalonate (700 mg) in anhydrous ethanol (6 ml) was added. Further, a solution of 2-aminothiazoline (265 mg) in anhydrous ethanol (2 ml) was added. With stirring, the mixture was heated under reflux for 5 hours. Water (50 ml) was added, and the mixture was washed with ether (30 ml). Conc. hydrochloric acid was added to the aqueous layer to adjust its pH to about 2. The aqueous layer was extracted with ethyl acetate (50 ml) twice. The ethyl acetate layers were combined, washed with a saturated aqueous solution of sodium chloride (50 ml) and dried over anhydrous sodium sulfate. Distilling off the solvent under reduced pressure gave 440 mg (yield 61%) of the compound No. 112 which had the following properties.

Melting point: 258°–216° C.

IR ($\nu_{max}^{KBr}$) cm$^{-1}$: 3380, 3200–2200 (enol form), 1660, 1624, 1592, 1542, 1490, 1433, 1257, 1128, 826.

NMR ($\delta_{TmS}^{DMSO-d6}$): 3.58 (2H, t, J=8Hz), 4.37 (2H, t, J=8Hz), 6.58 (2H, d, J=9Hz), 6.90 (1H, br; disappeared in D$_2$O), 7.14 (2H, d, J=9Hz), 10.3–12.0 (1H, br; disappeared in D$_2$O; enol form).

EXAMPLE 2

Synthesis of 6-o-chloroanilino-5H,2,3,6,7-tetrahydro-5,7-dioxothiazolo[3,2-a]pyrimidine (No. 114):

o-Chloroaniline (15.9 g) was dissolved in dry toluene (20 ml), and diethyl bromomalonate (12.0 g) was added. The mixture was heated under reflux with stirring for 10 hours. The reaction mixture was washed with dilute hydrochloric acid, then with water three times, and dried over anhydrous sodium sulfate. The solvent was distilled off under reduced pressure. The residue was purified by silica gel column chromatography using benzene as an eluent to give 5.1 g (yield 36%) of diethyl o-chloroanilinomalonate which had the following NMR data.

NMR ($\delta_{TMS}^{CDCl3}$): 1.20 (6H, t, J=8Hz), 4.17 (4H, q, J=7Hz), 4.57 (1H, d, J=7Hz), 5.40 (1H, d, J=7Hz), 6.3–7.3 (4H, m).

(2) Synthesis of compound No. 114

Metallic sodium (0.28 g) was added to anhydrous ethanol (10 ml) to prepare a solution of sodium ethoxide in ethanol, and diethyl o-chloroanilinomalonate (2.86 g) and 2-aminothiazoline (1.02 g) were added. With stirring, the mixture was heated under reflux for 5 hours. Water (50 ml) and ethyl acetate (30 ml) were added, and thereafter, dilute hydrochloric acid was added to adjust the pH of the mixture to about 4. The solid which precipitated was collected by filtration, washed with water, and recrystallized from ethanol to give 0.92 g (yield 31%) of the compound No. 114 having the following properties.

Melting point: 247.0°–249.5° C.

IR ($\nu_{max}^{KBr}$) cm$^{-1}$: 3380, 3100–2000 (enol form) 1635, 1598, 1580, 1530, 1400, 1355, 1313, 1257, 758.

NMR ($\delta$ DMSO—d$_6$) ppm: CDCl$_3$ TMS 3.53 (2H, t, J=7Hz), 4.40 (2H, t, J=7Hz), 5.53 (1H, br; disappeared when D$_2$O was added), 6.3–7.4 (4H, m), 10.5–12.0 (1H, br; disappeared when D$_2$O was added).

EXAMPLE 3

Synthesis of 6-m-chloroanilino-5H-2,3,6,7-tetrahydro-5,7-dioxothiazolo[3,2-a]pyrimidine (No. 116):

(1) Synthesis of diethyl m-chloroanilinomalonate m-Chloroaniline (12.8 g) and diethyl bromomalonate (9.6 g) were dissolved in dry toluene (20 ml). The solution was heated under reflux with stirring for 3 hours. The reaction mixture was washed with dilute hydrochloric acid and then three times with water, and dried over anhydrous sodium sulfate. The solvent was distilled off under reduced pressure. The residue was washed with n-hexane to give 3.3 g (yield 29%) of diethyl m-chloroanilinomalonate having the following NMR data.

NMR ($\delta_{TMS}^{CDCl3}$) ppm: 1.25 (6H, t, J=7Hz), 4.20 (4H, q, J=7Hz), 4.5–4.7 (2H, br; 1H when D$_2$O was added), 6.2–7.3 (4H, m).

(2) Synthesis of compound No. 116

Metallic sodium (0.29 g) was added to anhydrous ethanol (10 ml) to prepare a solution of sodium ethoxide in ethanol and diethyl m-chloroanilinomalonate (2.86 g) and then 2-aminothiazoline (1.02 g) were added. With stirring, the mixture was heated under reflux for 5 hours. Water (50 ml) and ethyl acetate (30 ml) were added, and then dilute hydrochloric acid was added to adjust the pH of the mixture to about 4. The solid which precipitated was collected by filtration, washed with water, and recrystallized from ethanol to give 0.76 g (yield 26%) of the compound No. 116 having the following properties.

Melting point: 269.0°–271.0° C.

IR ($\nu_{max}^{KBr}$) cm$^{-1}$: 3300, 3150–2000 (enol form) 1635, 1600, 1530, 1515, 1425, 1410, 1395, 1360, 1135, 770.

NMR ($\delta$ DMSO—d$_6$) ppm: CDCl$_3$ TMS 3.57 (2H, t, J=7Hz), 4.40 (2H, t, J=7Hz), 5.43 (1H, br; disappeared when D$_2$O was added), 6.7–7.1 (4H, m), 10.5–12.0 (1H, br; disappeared when D$_2$O was added).

EXAMPLE 4

Synthesis of 6-anilino-5H-2,3,6,7-tetrahydro-5,7-dioxothiazole[3,2-a]pyrimidine (No.110):

(1) Synthesis of diethyl anilinomalonate

Aniline (18.6 g) was dissolved in dry benzene (125 ml), and diethyl bromomalonate (23.9 g) was added. The mixture was heated under reflux for 37 hours with stirring. The reaction mixture was washed with dilute hydrochloric acid to remove the unreacted aniline. The benzene layer was washed with water three times, and dried over anhydrous magnesium sulfate. The solvent was distilled off under reduced pressure. The residue was purified by silica gel column chromatography using hexane/ethyl acetate (10:1) as an eluent to give 7.5 g (yield 30%) of diethyl anilinomalonate having the following NMR data.

NMR ($\delta_{TMS}^{CCl4}$): 1.20 (6H, t, J=7Hz), 4.20 (4H, q, J=7Hz), 4.66 (2H, s, br; 1H when D$_2$O was added), 6.5–7.3 (5H, m).

(2) Synthesis of compound No. 110

Metallic sodium (0.80 g) was added to anhydrous ethanol (30 ml) to prepare a solution of sodium ethoxide in ethanol, and a solution of diethyl anilinomalonate (3.75 g) in anhydrous ethanol (15 ml) and then 2-aminothiazoline (1.52 g) were added to the solution. With stirring, the mixture was heated under reflux for 2.5 hours. When the reaction mixture was allowed to cool, a solid precipitated. The solid (3.7 g) was then separated by filtration. A portion (1.20 g) of the solid was dissolved in water, and the pH of the solution was adjusted to about 4 to precipitate a solid. The solid was washed with water and dried to give 0.26 g (yield 24%) of the compound No. 110 having the following properties.

Melting point: 226.0°–228.0° C.

IR ($\nu_{max}^{KBr}$) cm$^{-1}$: 3020, 1680, 1500, 1390, 1340, 1300, 1258, 1122.

NMR ($\delta_{TMS}^{CCl4}$) ppm: 3.60 (2H, t, J=7Hz), 4.37 (2H, t, J=7Hz), 6.4–7.5 (6H, m; in D$_2$O, 1H disappeared), 10.0–11.5 (1H, br; disappeared in D$_2$O; enol form).

EXAMPLE 5

Synthesis of 6-benzylamino-5H,2,3,6,7-tetrahydro-5,7-dioxothiazolo[3,2-a]pyrimidine (No. 138):

(1) Synthesis of diethyl benzylaminomalonate

Benzylamine (18.3 g) and diethyl bromomalonate (20.3 g) were dissolved in dry benzene (100 ml), and the mixture was heated under reflux for 14 hours with stirring. The precipitated salt was removed by filtration from the reaction mixture. The filtrate was washed with dilute hydrochloric acid to remove the unreacted benzylamine. The benzene layer was washed with water three times, and dried over anhydrous magnesium sulfate. The solvent was distilled off under reduced pressure. The residue was purified by silica gel column chromatography using hexane/ethyl acetate (4:1) as an eluent to give 4.7 g (yield 21%) of diethyl benzylaminomalonate having the following NMR data.

NMR ($\delta_{TMS}^{CCl4}$): 1.22 (6H, t, J=7Hz), 3.20 (2, H, s), 4.10 (4H, q, J=7Hz), 4.70 (2H, s, br; 1H when D$_2$O was added), 7.15–7.5 (5H, m).

(2) Synthesis of compound No. 138

Metallic sodium (0.46 g), diethyl benzylaminomalonate (2.65 g), 2-aminothiazoline (1.20 g) and anhydrous ethanol (20 ml) were used, and otherwise, the same procedure as in Example 4. (2), was repeated. The residue was purified by silica gel column chromatography using methylene chloride/methanol (19:1) as an eluent to give 0.8 g (yield 29%) of the compound No. 138 having the following properties.

Melting point: 196.0°–198.0° C.

IR ($\nu_{max}^{KBr}$) cm$^{-1}$: 3200–2000 (enol form) 1600, 1590, 1375, 1240, 1120, 1070.

NMR ($\delta_{TMS}^{CCl4}$) ppm: 3.30 (2H, t, J=7Hz), 4.23 (2H, t, J=7Hz), 4.23 (2H, s), 7.1–7.5 (6H, m; 5H when D$_2$O was added), 10.0–11.5 (1H, br; disappeared when D$_2$O was added; enol form).

EXAMPLE 6

Synthesis of 5H-2,3,6,7-tetrahydro-6-(N-methylanilino)-5,7-dioxothiazolo[3,2-a]pyrimidine (No. 164):

(1) Synthesis of diethyl N-methylanilinomalonate:

N-methylaniline (15.1 g), diethyl bromomalonate (16.9 g) and dry benzene (90 ml) were mixed and heated under reflux for 16 hours with stirring. The reaction mixture was washed, dried and concentrated by the same procedure as in Example 2, (1). The residue was purified by silica gel column chromatography using benzene/hexane (2:1) as an eluent to give 10.2 g (yield 54%) of diethyl N-methylanilinomalonate having the following NMR data.

NMR ($\delta_{TMS}^{CCl4}$) ppm: 1.23 (6H, t, J=7Hz), 3.02 (3H, s), 4.20 (4H, q, J=7Hz), 5.03 (1H, s), 6.6–7.45 (5H, m).

(2) Synthesis of compound No. 164

Diethyl N-methylanilinomalonate (1.58 g), 2-aminothiazoline (0.71 g) and diphenyl ether (2 ml) were mixed, and heated with stirring at 175° C. for 1.5 hours in an atmosphere of nitrogen. The reaction mixture was chromatographed on a silica gel column using methylene chloride/methanol (19:1) as an eluent to give 0.43 g (yield 27%) of the compound No. 164 having the following properties.

Melting point: 100.0°–102.0° C.

IR ($\nu_{max}^{KBr}$) cm$^{-1}$: 3700–2000 (enol form), 1635, 1602, 1505, 1400

NMR ($\delta_{TMS}^{CDCl3}$) ppm: 3.03 (3H, s), 3.35 (2H, t, J=7Hz), 4.30 (2H, t, J=7Hz), 6.45–7.5 (5H, m), 10.0–11.5 (1H, br; disappeared when D$_2$O was added; enol form).

EXAMPLE 7

Synthesis of 6-(p-chloro-N-methylanilo)-5H-2,3,6,7-tetrahydro-5,7-dioxothiazolo[3,2-a]pyrimidine (No. 166):

(1) Synthesis of diethyl p-chloro-N-methylanilinomalonate p-Chloro-N-methylaniline (10.1 g), diethyl bromomalonate (8.5 g) and dry benzene (60 ml) were mixed, and heated under reflux for 7 hours with stirring. The reaction mixture was washed, dried and concentrated by the same procedure as in Example 2, (1). The residue was chromatographed on a silica gel column using benzene/hexane (1:1) as an eluent to give 3.5 g (yield 33%) of diethyl p-chloro-N-methylanilinomalonate having the following NMR data.

NMR ($\delta_{TMS}^{CCl4}$): 1.30 (6H, t, J=7Hz), 3.00 (3H, s), 4.25 (4H, q, J=7Hz), 4.95 (1H, s), 6.72 (2H, d, J=9Hz), 7.21 (2H, d, J=9Hz).

(2) Synthesis of compound No. 166

Diethyl p-chloro-N-methylanilinomalonate (2.40 g), 2-aminothiazoline (0.98 g) and diphenyl ether (5 ml) were mixed, and heated at 180° C. for 2 hours with stirring in an atmosphere of nitrogen. The residue was washed with methylene chloride to give 0.99 g (yield 36%) of the compound No. 166 having the following properties.

Melting point: 228.0°–230.5° C.

IR ($\nu_{max}^{KBr}$) cm$^{-1}$: 3700–2000 (enol form), 1620, 1600, 1525, 1497, 1405, 1360, 1250, 1120.

NMR ($\delta$ CDCl$_3$+DMSO—d$_6$) ppm: TMS 3.03 (3H, s), 3.53 (2H, t, J=7Hz), 4.37 (2H, t, J=7Hz), 6.50 (2H, d, J=9Hz), 7.06 (2H, d, J=9Hz), 10.0–11.5 (1H, br; disappeared when D$_2$O was added; enol form).

EXAMPLE 8

Synthesis of 5H-2,3-dihydro-7-methoxy-6-(N-methylanilino)-5-oxothiazolo[3,2-a]pyrimidine (No. 208) and 6-anilino-5H-2,3-dihydro-7-methoxy-5-oxothiazolo[3,2-a]pyrimidine (No. 204):

Sodium hydride (0.2 g) was suspended in anhydrous dimethyl formamide (10 ml), and a solution of 1.7 g of the 6-anilino-5H-2,3,6,7-tetrahydro-5,7-dioxothiazolo[3,2-a]-pyrimidine obtained in Example 4 in anhydrous dimethyl formamide (5 ml) was added. Further, methyl iodide (3.0 g) was added, and the mixture was stirred at room temperature for 8 hours. The solvent was removed by concentration under reduced pressure, and the residue was extracted with chloroform. The chloroform layer was washed with water, and dried over anhydrous sodium sulfate. The solvent was distilled off. The residue was chromatographed on a silica gel column using chloroform/methanol (20:0-1). There were obtained 0.26 g (yield 15%) of 5H-2,3-dihydro-7-methoxy-6-(N-methylanilino)-5-oxothiazolo[3,2-a]pyrimidine (No. 208) from a fraction having low polarity and 0.18 g (yield 10%) of 6-anilino-5H-2,3-dihydro-7-methoxy-5-oxothiazolo[3,2-a]pyrimidine (No. 204) from a fraction having high polarity. The properties of these products were as follows:

Compound No. 208

Melting point: 234.5°–237.0° C.

IR $(\nu_{max}^{KBr})$ cm$^{-1}$: 1658, 1580, 1520, 1503, 1468, 1395, 1360, 1345, 1238, 1125, 760.

NMR $(\delta_{TMS}^{CDCl_3})$ ppm: 3.13 (3H, s), 3.46 (2H, t, J=7Hz), 3.90 (3H, s), 3.50 (2H, t, J=7Hz), 6.6–7.5 (5H, m).

Compound No. 204

IR $(\nu_{max}^{KBr})$ cm$^{-1}$: 1655, 1595, 1525, 1497, 1460, 1393, 1345, 1320, 1265, 1145, 963, 742.

NMR $(\delta_{TMS}^{CDCl_3})$ ppm: 3.44 (2H, t, J=7Hz), 3.93 (3H, s), 4.45 (2H, t, J=7Hz), 5.3 (1H, br s; disappeared when D$_2$O was added) 6.6–7.5 (5H, m).

EXAMPLE 9

Synthesis of 6-(p-chloro-N-methylanilino)-5H,2,3-dihydro-7-methoxy-5-oxothiazo[3,2-a]pyrimidine (No. 210) and 6-p-chloroanilino-5H-2,3-dihydro-7-methoxy-5-oxothiazolo[3,2-a]pyrimidine (No. 206):

The 6-chloroanilino-5H-2,3,6,7-tetrahydro-5,7-dioxothiazolo[3,2-a]pyrimidine obtained in Example 1 was converted to a sodium salt (390 mg) in the same way as in Example 20 given hereinbelow. The sodium salt was then dissolved in 5 ml of anhydrous dimethyl formamide, and then 1 ml of methyl iodide was added. The mixture was stirred at room temperature for 12 hours. After the reaction, the reaction mixture was worked up in the same way as in Example 8. The residue was subjected to thin-layer chromatography and developed with methylene chloride/methanol (19:1). There were obtained 85 mg (yield 23%) of the compound No. 210 from a fraction having an Rf value of 0.47, and 25 mg (yield 7%) of the compound No. 206 from a fraction having an Rf value of 0.4. The properties of these products were as follows:

Compound No. 210

Melting point: 165.5°–165.6° C.

IR $(\nu_{max}^{KBr})$ cm$^{-1}$: 1645, 1580, 1523, 1498, 1460, 1400, 1350, 1238, 1120, 820.

NMR $(\delta_{TMS}^{CDCl_3})$ ppm: 3.07 (3H, s), 3.43 (2H, t, J=7Hz), 3.86 (3H, s), 4.43 (2H, t, J=7Hz), 6.75–7.3 (4H, m).

Compound No. 206

Melting point: 184.0°–186.5° C.

IR $(\nu_{max}^{KBr})$ cm$^{-1}$: 1640, 1580, 1495, 1448, 1390, 1345, 1320, 1260, 1200, 1148, 964, 815.

NMR $(\delta_{TMS}^{CDCl_3})$ ppm: 3.45 (2H, t, J=7Hz), 3.88 (3H, s), 4.45 (2H, t, J=7Hz), 5.35 (1H, s; disappeared when D$_2$O was added), 6.45–7.3 (4H, m).

EXAMPLE 10

Synthesis of 7-n-butoxy-6-(N-n-butylanilino)-5H-2,3-dihydro-5-oxothiazolo[3,2-a]pyrimidine (No. 212) and 6-anilino-7-n-butoxy-5H-2,3-dihydro-5-oxothiazolo-[3,2-a]pyrimidine (No. 214):

Sodium hydride (0.17 g) was suspended in anhydrous dimethyl formamide (20 ml), and a solution of 1.50 g of the 6-anilino-5H-2,3,6,7-tetrahydro-5,7-dioxothiazolo-[3,2-a]pyrimidine obtained in Example 4 in 5 ml of anhydrous dimethyl formamide was added. Then, n-butyl bromide was added. The mixture was stirred at 15° to 20° C. for 8 hours. After the reaction, the reaction mixture was worked up in the same way as in Example 8. The residue was chromatographed on a silica gel column using methylene chloride/hexane (1:1–0) as an eluent. There were obtained 0.09 g (yield 4%) of the compound No. 212 from a fraction having low polarity, and 0.76 g (yield 42%) of the compound No. 214 from a fraction having high polarity. The properties of these products are as shown below.

Compound No. 212

Melting point: 119.0°–121.5° C.

IR $(\nu_{max}^{KBr})$ cm$^{-1}$: 1650, 1577, 1513, 1498, 1395, 1338, 1240, 753.

NMR $(\delta_{TMS}^{CDCl_3})$ ppm: 3.46 (4H, t, J=7Hz), 4.20 (2H, t, J=7Hz), 4.46 (2H, t, J=7Hz), 0.6–2.0 (14H, m), 6.43–7.4 (5H, m).

Compound No. 214

Melting point: 97.0°–98.5° C.

IR $(\nu_{max}^{KBr})$ cm$^{-1}$: 1640, 1590, 1500, 1460, 1390, 1325, 1260, 1148.

NMR $(\delta_{TMS}^{CDCl_3})$ ppm: 0.6–1.9 (7H, m), 3.41 (2H, t, J=8Hz), 4.30 (2H, t, J=7Hz), 4.43 (2H, t, J=8Hz), 5.38 (1H, s; disappeared when D$_2$O was added), 6.6–7.5 (5H, m).

EXAMPLE 11

Synthesis of 6-(N-allylanilino)-7-allyloxy-5H,2,3-dihydro-5-oxothiazolo[3,2-a]pyrimidine (No. 232) and 7-allyloxy-6-anilino-5H-2,3-dihydro-5-oxothiazolo-[3,2-a]pyrimidine (No. 234):

Sodium hydride (0.12 g) was suspended in anhydrous dimethyl formamide (10 ml), and a solution of the 6-anilino-5H,2,3,6,7-tetrahydro-5,7-dioxothiazolo[3,2-a]pyrimidine (0.52 g) in anhydrous dimethyl formamide (5 ml) was added. Then, 0.29 g of allyl bromide was added. The mixture was stirred at 15° to 20° C. for 30 hours. After the reaction, the reaction mixture was worked up in the same way as in Example 8. The residue was subjected to silica gel thin-layer chromatography and developed with methylene chloride/methanol (19:1). There were obtained 0.15 g (yield 25%) of the compound No. 232 from a fraction having low polarity, and 0.07 g (yield 11%) of the compound No. 234 form a fraction having high polarity. The properties of these products are shown below.

Compound No. 232

Melting point: 134.0°–136.0° C.

IR $(\nu_{max}^{KBr})$ cm$^{-1}$: 1650, 1578, 1515, 1500, 1392, 1335, 1298, 1227, 1143, 755.

NMR ($\delta_{TMS}^{CDCl_3}$) ppm: 3.40 (2H, t, J=7Hz), 4.06 (2H, d, J=4Hz), 4.40 (2H, t, J=7Hz), 4.70 (2H, d, J=4Hz), 4.73-5.50 (4H, m), 6.5-7.33 (5H, m).

Compound No. 234

Melting point: 123.0°-124.5° C.

IR ($\nu_{max}^{KBr}$) cm$^{-1}$: 1655, 1595, 1515, 1498, 1395, 1335, 1320, 1260, 1140.

NMR ($\delta_{TMS}^{CDCl_3}$) ppm: 3.40 (2H, t, J=8Hz), 4.43 (2H, t, J=8Hz), 4.85 (2H, d, J=5Hz), 5.0-5.6 (3H, m; 2H when D$_2$O was added), 5.65-6.5 (1H, m), 6.6-7.4 (5H, m).

The above reaction simultaneously yielded 6-(N-allylanilino)-5H-2,3,6,7-tetrahydro-5,7-dioxothiazolo-[3,2-a]pyrimidine (No. 174) which had the following properties.

Melting point: 108.5°-112.0° C.

IR ($\nu_{max}^{KBr}$) cm$^{-1}$: 3700-2000 (enol), 1640, 1602, 1503, 1402, 1240, 1225, 1022.

NMR ($\delta_{TMS}^{CDCl_3}$) ppm: 3.41 (2H, t, J=8Hz), 4.15 (2H, d, J=7Hz), 4.40 (2H, t, J=8Hz), 5.0-5.6 (2H, m), 5.7-6.4 (1H, m), 6.6-7.9 (5H, m), 10.5-12.0 (1H, br; disappeared when D$_2$O was added; enol form).

EXAMPLE 12

Synthesis of 7-benzyloxy-6-(N-benzyl-N-phenylamino)-5H-2,3-dihydro-5-oxothiazolo[3,2-a]pyrimidine (No. 260) and 6-anilino-7-benzyloxy-5H-2,3-dihydro-5-oxothiazolo[3,2-a]pyrimidine (No. 258):

Sodium hydride (0.28 g) was suspended in anhydrous dimethyl formamide (20 ml), and a solution of the 6-anilino-5H 2,3,6,7-tetrahydro-5,7-dioxothiazolo[3,2-a]pyrimidine (2.50 g) obtained in Example 4 in anhydrous dimethyl formamide (10 ml) was added. Then, 2.48 g of benzyl chloride was added. The mixture was stirred at 15° to 20° C. for 8 hours. After the reaction, the reaction mixture was worked up in the same way as in Example 8. The residue was chromatographed on a silica gel column using methylene chloride/methanol (15:0-1) as an eluent. There were obtained 0.32 g (yield 8%) of the compound No. 260 from a fraction having low polarity, and 0.94 g (yield 28%) of the compound No. 258 from a fraction having high polarity. The properties of these products are shown below.

Compound No. 260

Melting point: 156.0°-158.0° C.

IR ($\nu_{max}^{KBr}$) cm$^{-1}$: 1650, 1583, 1518, 1500, 1392, 1355, 1228, 1143, 758.

NMR ($\delta_{TMS}^{CDCl_3}$) ppm: 3.30 (2H, t, J=7.5 Hz), 4.35 (2H, t, J=7.5 Hz), 4.75 (2H, s), 5.29 (2H, s), 6.45-7.6 (1.5H, m).

Compound No. 258

Melting point: 160.0°-161.0° C.

IR ($\nu_{max}^{KBr}$) cm$^{-1}$: 1640, 1603, 1585, 1505, 1440, 1392, 1345, 1265, 1150.

NMR ($\delta_{TMS}^{CDCl_3}$) ppm: 3.36 (2H, t, J=8 Hz), 4.40 (2H, t, J=8 Hz), 5.4 (3H, s; 2H when D$_2$O was added), 6.57-7.5 (10H, m).

EXAMPLE 13

Synthesis of 5H-2,3-dihydro-5-methoxy-6-(N-methylanilino)-7-oxothiazolo[3,2-a]pyrimidine (No. 304):

A sodium salt of the enolate of 6-anilino-5H-2,3,6,7-tetrahydro-5,7-dioxothiazolo[3,2-a]pyrimidine (0.97 g) was dissolved in anhydrous N,N-dimethyl formamide (25 ml), and methyl iodide (2.0 g) was added. The mixture was stirred at 15° C. for 22 hours. The solvent was distilled off under reduced pressure, and the residue was chromatographed on a silica gel column using methylene chloride/methanol (20:1-2) as an eluent to give 0.32 g (yield 13%) of the compound No. 304 having the following properties.

Melting point: 124.0°-127.5° C.

IR ($\nu_{max}^{KBr}$) cm$^{-1}$: 1640, 1600, 1555, 1505, 1325, 1250, 753.

NMR ($\delta_{TMS}^{CDCl_3}$) ppm: 3.13 (3H, s), 3.33 (2H, t, H=8 Hz), 3.43 (3H, s), 4.47 (2H, t, J=8 Hz), 6.5-7.2 (5H, m).

EXAMPLE 14

Synthesis of 6-anilino-5-benzyloxy-5H-2,3-dihydro-7-oxothiazolo[3,2-a]pyrimidine (No. 314):

6-Anilino-5H-2,3,6,7-tetrahydro-5,7-dioxothiazolo[3,2-a]pyrimidine (2.50 g) was added to a suspension of sodium hydride (0.28 g) in anhydrous N,N-dimethylformamide (20 ml). Furthermore, benzyl chloride (2.48 g) was added, and the mixture was stirred at 20° C. for 14 hours. The solvent was distilled off under reduced pressure. The residue was extracted with ethyl acetate, washed with water, dried over anhydrous sodium sulfate, and concentrated. The residue was chromatographed on a silica gel column using methylene chloride as an eluent to give 0.30 g (yield 9%) of the compound No. 314 having the following properties.

Melting point: 198°-200.5° C.

IR ($\nu_{max}^{KBr}$) cm$^{-1}$: 1623, 1540, 1470, 1447, 1425, 1320, 1293, 1240, 766, 715.

NMR ($\delta_{TMS}^{CDCl_3}$) ppm: 3.20 (2H, t, J=7 Hz), 4.33 (2H, t, J=7 Hz), 5.00 (2H, s), 6.4-7.4 (11H, m).

EXAMPLE 15

Synthesis of 7-acetoxy-6-(N-acetyl-N-phenylamino)-5H-2,3-dihydro-5-oxothiazolo[3,2-a]pyrimidine (No. 278):

6-Anilino-5H-2,3,6,7-tetrahydro-5,7-dioxothiazolo[3,2-a]pyrimidine obtained in Example 4 (1.0 g), acetic anhydride (0.47 g), triethylamine (0.58 g) and methylene chloride (50 ml) were mixed, and stirred at 15° to 20° C. for 8 hours. The reaction mixture was washed with a saturated aqueous solution of sodium bicarbonate and then three times with water, and dried over anhydrous sodium sulfate. The solvent was then distilled off under reduced pressure. The residue was chromatographed on a silica gel column using methylene chloride/methanol (25:0-1) to give 0.10 g (yield 8%) of the compound No. 278 having the following properties.

IR ($\nu_{max}^{KBr}$) cm$^{-1}$: 1793, 1665, 1600, 1530, 1395, 1345, 1320, 1180, 1008.

NMR ($\delta_{TMS}^{CDCl_3}$) ppm: 2.06 (3H, s), 2.20 (3H, s), 3.52 (2H, t, J=7 Hz), 4.50 (2H, t, J=7 Hz), 7.4 (5H, br s).

EXAMPLE 16

Synthesis of 6-(N-benzoyl-N-phenylamino)-5H-2,3,6,7-tetrahydro-5,7-dioxothiazolo[3,2-a]pyrimidine (No. 178):

6-Anilino-5H-2,3,6,7-tetrahydro-5,7-dioxothiazolo[3,2-a]pyrimidine (1.67 g) was suspended in methylene chloride (20 ml), and triethylamine (1.52 g) was added. Subsequently, benzoyl chloride (1.83 g) was added. The mixture was stirred at 10° to 20° C. for 15 hours. After the reaction, the reaction mixture was washed with dilute hydrochloric acid and then with a saturated aqueous solution of sodium bicarbonate, and then three times with water. The methylene chloride layer was dried over anhydrous magnesium sulfate, and the solvent was distilled off under reduced pressure. The residue was chromatographed on a silica gel column using methylene chloride/methanol (49:1) as an eluent to give 1.19 g (yield 51%) of the compound No. 178 having the following properties.

Melting point: 100.0°–102.0° C.

IR ($\delta_{max}^{KBr}$) cm$^{-1}$: 3700-2050 (enol), 1758, 1685, 1660, 1600, 1530, 1498, 1396, 1342, 1243, 1100.

NMR ($\delta_{TMS}^{CDCl_3}$) ppm: 3.50 (2H, t, J=7 Hz), 4.50 (2H, t, J=7 Hz), 7.1–7.8 (8H, m), 7.9–8.3 (2H, m), 10.5–12.0 (1H, br; disappeared when D$_2$O was added; enol form).

EXAMPLE 17

Synthesis of 6-(N-cyclohexyl-N-methylamino)-5H-2,3-dihydro-7-hydroxy-5-oxothiazolo[3,2-a]pyrimidine sodium salt (No. 267):

(1) Synthesis of diethyl (N-cyclohexyl-N-methylamino)-malonate

Diethyl bromomalonate (17.0 g), triethylamine (9.1 g), and dry toluene (10 ml) were mixed, and with stirring, the mixture was heated under reflux. Then, N-cyclohexyl-N-methylamine (8.1 g) diluted with dry toluene (5 ml) was added dropwise, and the mixture was heated under reflux for 2.5 hours with stirring. The reaction mixture was washed with water three times, and dried over anhydrous sodium sulfate, and the solvent was distilled off under reduced pressure. The residue was distilled under reduced pressure to give 5.5 g (29%) of diethyl (N-cyclohexyl-N-methylamino)malonate having the following properties.

Boiling point: 124° -128° C. (0.4 mmHg)

NMR ($\delta_{TMS}^{CDCl_3}$) ppm: 1.23 (6H, t, J=7 Hz), 0.9–2.1 (10H, m), 2.42 (3H, s), 2.3–3.0 (1H, m), 4.31 (4H, q, J=7 Hz), 4.06 (1H, s).

(2) Synthesis of compound No. 267

Metallic sodium (0.30 g) was dissolved in anhydrous ethanol (10 ml), and diethyl N-cyclohexyl-N-methylaminomalonate (2.7 g) was added. Then, 2-aminothiazoline (1.0 g) was added. The mixture was heated under reflux for 3 hours with stirring. The solid which precipitated was collected by filtration, and washed with ethanol to give 0.86 g (yield 31%) of the compound No. 267 having the following properties.

IR ($\nu_{max}^{KBr}$) cm$^{-1}$: 1635, 1562, 1505, 1400, 1238,

NMR ($\delta_{DSS}^{D_2O}$) ppm: 0.9–2.1 (10H, m), 2.90 (3H, s), 2.8–3.0 (1H, br), 3.50 (2H, t, J=8 Hz), 4.35 (2H, t, J=8 Hz).

EXAMPLE 18

Synthesis of 5H-2,3-dihydro-7-hydroxy-5-oxo-6-di-n-propylamino-thiazolo[3,2-a]pyrimidine sodium salt (No. 268):

(1) Synthesis of diethyl di-n-propylaminoalonate

Di-n-propylamine (15.2 g) and diethyl bromomalonate (17.9) were dissolved in dry benzene (90 ml), and the mixture was heated under reflux for 7 hours with stirring. The reaction mixture was worked up in the same way as in Example 2, (1). The resulting residue was chromatographed on a silica gel column using benzene/ethyl acetate (20:1) as an eluent to give 16.9 g (yield 87%) of diethyl di-n-propylaminomalonate.

(2) Synthesis of compound No. 268

Metallic sodium (0.28 g) was added to anhydrous ethanol (10 ml) to prepare a solution of sodium ethoxide in ethanol. A solution of diethyl di-n-propylaminomalonate (2.74 g) in anhydrous ethanol (10 ml) was added, and 2-aminothiazoline (1.02 g) was further added. The mixture was heated under reflux for 3 hours with stirring. The solid which precipitated was collected by filtration, and washed with ethanol to give 0.74 g (yield 26%) of the compound No. 268 having the following properties.

IR ($\nu_{max}^{KBr}$) cm$^{-1}$: 1637, 1563, 1518, 1415, 1400, 1225, 797.

NMR ($\delta_{DSS}^{D_2O}$) ppm: 0.80 (3H, t, J=7 Hz), 1.15 (3H, t, J=7 Hz), 0.15–1.6 (4H, m), 2.9 (2H, t, J=8 Hz), 3.45 (2H, t, J=8 Hz), 3.57 (2H, t, J=7 Hz), 4.30 (2H, t, J=7 Hz).

EXAMPLE 19

Synthesis of 6-anilino-5H-2,3-dihydro-7-hydroxy-5-oxothiazolo[3,2-a]pyrimidine sodium salt (No. 299):

6-Anilino-5H-2,3,6,7-tetrahydro-5,7-dioxo-thiazolo[3,2-a]pyrimidine (No. 110) (1.31 g) was added to sodium hydroxide (0.2 g) and water (3 ml), and the mixture was stirred at room temperature to form a solution. Water was distilled off under reduced pressure to give 1.4 g (yield 100%) of the compound No. 299 having the following NMR data.

NMR ($\delta_{DSS}^{D_2O}$) ppm: 3.53 (2H, t, J=7 Hz), 4.27 (2H, t, J=7 Hz), 6.5–7.4 (5H, m).

EXAMPLE 20

Synthesis of 6-p-chloroanilino-5H-2,3-dihydro-7-hydroxy-5-oxo-thiazolo[3,2-a]pyrimidine sodium salt (No. 269):

1.48 g of 6-p-chloroanilino-5H-2,3,6,7-tetrahydro-5,7-dioxothiazolo[3,2-a]pyrimidine (No. 112) was added to sodium hydroxide (0.2 g) and water (3 ml), and the mixture was stirred at room temperature for 1 hour to form a solution. Water was distilled off under reduced pressure to give 1.58 g (yield 100%) of the compound No. 269 having the following NMR data.

NMR ($\delta_{DSS}^{D_2O}$) ppm: 3.40 (2H, t, J=7 Hz), 4.27 (2H, t, J=7 Hz), 6.4–7.3 (4H, m).

EXAMPLE 21

Synthesis of 6-anilino-7-n-butoxy-5H-2,3-dihydro-5-oxothiazolo[3,2-a]pyrimidine-1-oxide (No. 410):

6-Anilino-7-n-butoxy-5H-2,3-dihydro-5-oxo-thiazolo[3,2-a]pyrimidine (450 mg) and m-chloro-perbenzoic acid (430 mg) were dissolved in methylene chloride (15 ml), and the solution was stirred at 20° C. for 21 hours. Then, the mixture was heated under reflux for 3 hours, and m-chloroperbenzoic acid (230 mg) was additionally supplied. The mixture was further heated under reflux for 3 hours. The reaction mixture was washed with a saturated aqueous solution of sodium bicarbonate twice, and then with water three times, and dried over anhydrous magnesium sulfate. The solvent was distilled off under reduced pressure. The residue was chromatographed on a silica gel column using methylene chloride/methanol (13:0-1) as an eluent to give 44 mg (yield 9%) of the compound No. 410 having the following properties.

IR ($\nu_{max}^{KBr}$) cm$^{-1}$: 1640, 1600, 1500, 1440, 1407, 1345, 1153, 1062, 740.

NMR ($\delta_{TMS}^{CDCl3}$) ppm: 0.6–1.85 (7H, m), 3.40 (2H, t, J=7 Hz), 4.43 (2H, t, J=6 Hz), 4.73 (2H, J=7 Hz), 6.6–7.6 (6H, m).

EXAMPLE 22

Synthesis of 6-p-chloroanilino-5H-2,3-dihydro-7-methoxy-5-oxo-thiazolo[3,2-a]pyrimidine-1-oxide (No. 406):

6-p-Chloroanilino-5H-2,3-dihydro-7-methoxy-5-oxothiazolo[3,2-a]pyrimidine (300 mg) and n-chloroperbenzoic acid (200 mg) were dissolved in methylene chloride (20 ml), and the solution was stirred at 20° C. for 6 hours. The reaction mixture was then worked up in the same way as in Example 21. The residue was chromatographed on a silica gel column using methylene chloride as an eluent to give 103 mg (yield 33%) of the compound No. 406 having the following properties.

NMR ($\delta_{TMS}^{CDCl3}$) ppm: 3.47 (2H, t, J=7 Hz), 4.00 (3H, s), 4.77 (2H, t, J=7 Hz), 6.05 (1H, br s), 6.6–7.4 (4H, m).

EXAMPLE 23

Synthesis of 5H-2,3-dihydro-7-methoxy-6-(N-methylanilino)-5-oxothiazolo[3,2-a]pyrimidine-1-oxide (No. 430):

5H-2,3-Dihydro-7-methoxy-6-(N-methylanilino)-5-oxothiazolo[3,2-a]pyrimidine (257 mg) and m-chloroperbenzoic acid (270 mg) were dissolved in 30 ml of methylene chloride, and the solution was stirred at 20° C. for 3 hours. Then, 30 ml of a saturated aqueous solution of sodium bicarbonate was added, and the mixture was stirred at the same temperature for 30 minutes. The methylene chloride solution was separated, washed with water, and dried over anhydrous sodium sulfate. The methylene chloride was removed under reduced pressure. The residue was chromatographed on a silica gel column using methylene chloride as an eluent to give 13 mg (yield 5%) of the compound No. 430 having the following NMR data.

NMR ($\delta_{TMS}^{CDCl3}$) ppm: 3.06 (3H, s), 3.33 (2H, t, J=6 Hz), 3.90 (3H, s), 4.60 (2H, t, J=6 Hz), 6.4–7.3 (5H, m).

EXAMPLE 24

Synthesis of 6-(p-Chloro-N-methylanilino)-5H-2,3-dihydro-7-methoxy-6-oxothiazolo[3,2-a]pyrimidine-1-oxide (No. 408):

6-(p-Chloro-N-methylanilino)-5H,2,3-dihydro-7-methoxy-5-oxothiazolo[3,2-a]pyrimidine (104 mg) and m-chloroperbenzoic acid (65 mg) were dissolved in methylene chloride (10 ml), and the solution was stirred at 20° C. for 6 hours. The reaction mixture was worked up in the same way as in Example 21. The residue was subjected to silica gel thin-layer chromatography and developed with methylene chloride to give 30 mg (yield 27%) of the compound No. 408 having the following NMR data.

NMR ($\delta_{TMS}^{CDCl3}$) ppm: 3.13 (3H, s), 3.46 (2H, t, J=7 Hz), 4.01 (3H, s), 4.70 (2H, t, J=7 Hz), 6.5–7.3 (4H, m).

EXAMPLE 25

Evaluation of delayed type hypersensitivity (DTH):

The effect of the compounds provided by the invention were evaluated in mice and rats.

(1) Male C3H mice aged 6 weeks old were used. The animals were sensitized by injection into the tail vein of $5 \times 10^5$ sheep red blood cells (SRBC) in 0.2 ml of saline. To assess DTH, the mice were challenged 4 days after immunization by subcutaneous injection of $10^8$ SRBC in 25 μl of saline into the right hind foot pad. The thickness of the foot was measured with a micrometer before challenge and again 24 hours afterwards. The difference between these two measurements is shown in 1/10 mm (foot pad reaction). The test compounds were administered orally before sensitization and 24, 48 and 72 hours afterwards. The results are shown in Table 1.

TABLE 1

| Treatment | Dose (mg/kg) | N | FPR (0.1 mm) |
|---|---|---|---|
| Control | — | 7 | 11.0 ± 1.6 |
| (No. 112) | 1 | 5 | 16.1 ± 1.1* |
|  | 5 | 5 | 12.5 ± 0.5 |
|  | 25 | 5 | 13.3 ± 1.2 |
| Control | — | 7 | 4.8 ± 0.6 |
| (No. 166) | 1 | 5 | 5.9 ± 2.3 |
|  | 5 | 5 | 3.7 ± 0.7 |
|  | 25 | 5 | 9.8 ± 2.4* |

*P < 0.05

(2) Male Sprague-Dawley rats aged 5–6 weeks old were used. The animals were sensitized with 0.2 ml of Freund's complete adjuvant (FCA) emulsion of $10^{10}$ Bordetella pertussis. To assess DTH, the rats were challenged 12 days after immunization by subcutaneous injection of $5 \times 10^9$ Bordetella pertussis in 0.1 ml of saline into the right hind foot pad. The percentage increase in foot volume was measured 24 and 48 hours after challenge. The test compounds were administered orally once daily from the 9th day to the 12th day. The results are shown in Table 2.

TABLE 2

| Treatment | Dose (mg/kg) | N | % increase in foot volume |
|---|---|---|---|
| Control | — | 11 | 37.7 ± 2.4 |
|  | 5 | 7 | 53.6 ± 8.3* |
|  | 25 | 7 | 52.1 ± 6.8* |

TABLE 2-continued

| Treatment | Dose (mg/kg) | N | % increase in foot volume |
|---|---|---|---|
| (No. 112) Control | | | |
| (structure: S-N-O ring with CH₃, N-methyl, phenyl-Cl substituent) | 5 | 7 | 40.5 ± 5.4 |
| | 25 | 7 | 53.3 ± 7.5* |
| (No. 166) | | | |

$*P < 0.05$

EXAMPLE 26

Plaque forming cells (PFC) test:

In vitro Spleen cells were prepared from female BALB/c mice aged 12 weeks old and suspended in RPMI-1640 medium cotaining 10% fetal calf serum (FCS). The cells were cultured in a culture dish with SRBC($2 \times 10^6$) for 5 days under 5% $CO_2$ in air by the modified method of Mischell and Dutton [Mischell, R. I. and Duttom, R. W.: J. Exp. Med. 126: 423 (1967)]. Plaque forming cells (PFC) were determined by Jerne's hemolytic plaque assay (Jerme, N. K. and Nardin, A. A.: Science 140: 405 (1963)). The results are shown in Table 3.

TABLE 3

| Treatment | Concentration (M) | PFC/culture (% of control) |
|---|---|---|
| Control | — | 100 |
| (No. 110) | $10^{-6}$ | 318 |
| | $10^{-5}$ | 466 |
| | $10^{-4}$ | 596 |
| (No. 302) | $10^{-6}$ | 342 |
| | $10^{-5}$ | 416 |
| | $10^{-4}$ | 288 |
| (No. 138) | $10^{-6}$ | 352 |
| | $10^{-5}$ | 172 |
| | $10^{-4}$ | 76 |

TABLE 3-continued

| Treatment | Concentration (M) | PFC/culture (% of control) |
|---|---|---|
| (No. 204) | $10^{-6}$ | 164 |
| | $10^{-5}$ | 151 |
| | $10^{-4}$ | 282 |
| (No. 206) | $10^{-6}$ | 150 |
| | $10^{-5}$ | 153 |
| | $3 \times 10^{-5}$ | 133 |
| (No. 112) Comparison | $10^{-6}$ | 700 |
| | $10^{-5}$ | 300 |
| | $10^{-4}$ | 8300 |
| (structure with 4-Cl benzyl) | $10^{-6}$ | 10 |
| | $10^{-5}$ | 50 |
| | $10^{-4}$ | 0 |
| (structure with 4-Br phenyl) | $10^{-4}$ | 50 |

EXAMPLE 27

Production of tablets:
Tablets were prepared each of which had the following composition.

| | |
|---|---|
| Active compound No. 112 | 50 mg |
| Lactose | 115 mg |
| Potato starch | 24 mg |
| Polyvinyl pyrrolidone | 10 mg |
| Magnesium stearate | 1 mg |

The active compound, lactose and potato starch were mixed, and the mixture was wetted uniformly with a 20% ethanol solution of polyvinyl pyrrolidone. The wet mixture was passed through a 20 mesh screen, and dried at 45° C. The particles were again passed through a 20 mesh screen. The granules were mixed with magnesium stearate and compressed into tablets.

EXAMPLE 28

Production of hard gelatin capsules:

Hard gelatin capsules were prepared each of which had the following composition.

| | |
|---|---|
| Active compound No. 110 | 50 mg |
| Microcrystalline cellulose | 75 mg |
| Lactose | 74 mg |
| Magnesium stearate | 1 mg |

The finely divided active compound, microcrystalline cellulose and non-pressed magnesium stearate were fully mixed. The mixture was filled into hard gelatin capsules.

What we claim is:

1. A compound selected from thiazolo[3,2-a]pyrimidines represented by the following general formula:

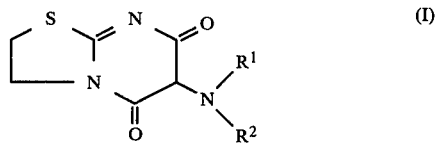

wherein $R^1$ and $R^2$ are identical or different, and each represents a hydrogen atom, an alkyl group having 1 to 10 carbon atoms, an alkenyl group having 3 to 10 carbon atoms, a substituted or unsubstituted phenyl group, a substituted or unsubstituted cycloaliphatic group having 3 to 8 carbon atoms, a substituted or unsubstituted phenylalkyl group or a substituted or unsubstituted acyl group having 2 to 7 carbon atoms, each of the above-mentioned substituted groups being substituted by a substituent selected from the group consisting of a halogen atom, a hydroxy group, a $C_{1-4}$ alkyl group which may be substituted by one or more halogen atoms, a $C_{1-4}$ alkoxy group which may be substituted by one or more halogen atoms, a nitrile group, a carboxyl group, and an alkoxycarbonyl group having 2 to 7 carbon atoms, provided that $R^1$ and $R^2$ are not simultaneously hydrogen atoms or substituted or unsubstituted acyl groups having 2 to 7 carbon atoms, or their enolate derivatives, or acid addition salts of these compounds.

2. The compound of claim 1 wherein in general formula (I), $R^1$ and $R^2$ are identical or different and each represents a hydrogen atom, an alkyl group having 1 to 6 carbon atoms, an alkenyl group having 3 to 6 carbon atoms, a substituted or unsubstituted phenyl group, a substituted or unsubstituted cycloaliphatic group having 5 or 6 carbon atoms, a substituted or unsubstituted phenyl ($C_{1-2}$) alkyl group, a substituted or unsubstituted aliphatic acyl group having 2 to 6 carbon atoms, or a substituted or unsubstituted benzoyl group, provided that $R^1$ and $R^2$ are not simultaneously hydrogen atoms, the substituted or unsubstituted aliphatic acyl groups having 2 to 6 carbon atoms or benzoyl groups.

* * * * *